United States Patent
Camp et al.

(10) Patent No.: US 8,314,092 B2
(45) Date of Patent: Nov. 20, 2012

(54) SUBSTITUTED [(5H-PYRROLO[2,1-C][1,4]BENZODIAZEPIN-11-YL)PIPERAZIN-1-YL]-2,2-DIMETHYLPROPANOIC ACID COMPOUNDS AS DUAL ACTIVITY H1 INVERSE AGONISTS/5-HT$_{2A}$ ANTAGONISTS

(75) Inventors: Anne Marie Camp, Basingstoke (GB); Peter Thaddeus Gallagher, Hampshire (GB); Andrew James Ledgard, Berkshire (DE); Adam Jan Sanderson, Camberley (GB); David Andrew Coates, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/357,627

(22) Filed: Jan. 25, 2012

(65) Prior Publication Data

US 2012/0202797 A1 Aug. 9, 2012

Related U.S. Application Data

(60) Provisional application No. 61/440,092, filed on Feb. 7, 2011.

(51) Int. Cl.
*A61P 25/20* (2006.01)
*A61K 31/5517* (2006.01)
*C07D 487/04* (2006.01)

(52) U.S. Cl. .................................. 514/220; 540/561
(58) Field of Classification Search .............. 514/220; 540/561
See application file for complete search history.

(56) References Cited

U.S. PATENT DOCUMENTS

| | | | |
|---|---|---|---|
| 4,192,803 A | 3/1980 | Wright, Jr. et al. | |
| 4,460,587 A | 7/1984 | Vlattas | |
| 4,507,311 A | 3/1985 | Vlattas | |
| 4,596,799 A | 6/1986 | Wasley | |

FOREIGN PATENT DOCUMENTS

| | | |
|---|---|---|
| WO | 2005103041 A2 | 11/2005 |
| WO | 2010142652 A1 | 12/2010 |

OTHER PUBLICATIONS

William B. Wright, Jr. et al.; Derivatives of 11-(1-Piperazinyl)-5H-pyrrolo[2,1-c][1,4]benzodiazepine as Central Nervous System Agents, J. Med. Chem. 1980, 462-465, 23.
Chih Y. Ho et al.; Indolo[2,1-c][1,4]benzodiazepines: A New Class of Antiallergic Agents, J. Med. Chem. 1986, 1118-1121, 29.
Abdelali Daich et al.; A Convenient Route to Diazepines by Inramolecular Cyclisation of Carbonylazides, J. Heterocyclic Chem., Dec. 1991, 1911-1915, 28.
A. J. Barbier et al.; Histaminergic Control of Sleep-Wake Cycles: Recent Therapeutic Advances for Sleep and Wake Disorders, CNS & Neurological Disorders—Drug Targets, 2007, 31-43, 6.
Stephen R. Morairty, Phd. et al., Selective 5HT2A and 5HT6 Receptor Antagonists Promote Sleep in Rats, Sleep, 2008, 34-44, vol. 31, No. 1.
Massimo Gianotti et al., Novel imidazobenzazepine derivatives as dual H1/5-HT2A antagonists for the treatment of sleep disorders, Bioorganic & Medicinal Chemistry Letters, 2010, 5069-5073, 20.

*Primary Examiner* — Brenda Coleman
(74) *Attorney, Agent, or Firm* — R. Craig Tucker

(57) ABSTRACT

A dual H1/5-HT$_{2A}$ receptor antagonist of the formula:

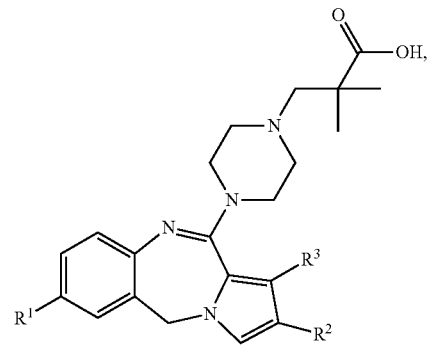

its uses, and methods for its preparation are described.

15 Claims, No Drawings

SUBSTITUTED [(5H-PYRROLO[2,1-C][1,4]BENZODIAZEPIN-11-YL)PIPERAZIN-1-YL]-2,2-DIMETHYLPROPANOIC ACID COMPOUNDS AS DUAL ACTIVITY H1 INVERSE AGONISTS/5-HT$_{2A}$ ANTAGONISTS

This application claims priority to U.S. provisional application Ser. No. 61/440,092, filed Feb. 7, 2011.

Histamine plays an important role in a variety of physiological processes through its interaction with at least four different G-protein coupled receptors, the H1-H4 receptors. In the CNS, H1 receptors play a key role in the sleep regulation cycle and H1 antagonists/inverse agonists are known to induce somnolence.

Likewise, serotonin plays important roles in a variety of physiological processes through its interaction with at least fourteen different G-protein coupled receptors. Modulation of 5-HT$_{2A}$ receptors in the CNS plays a key role in the sleep regulation cycle and 5-HT$_{2A}$ antagonists have been shown to improve slow wave sleep and sleep maintenance in patients with insomnia.

Compounds having H1 or 5-HT$_{2A}$ inverse agonist or antagonist activity have been used in the treatment of insomnia (e.g. doxepin and trazodone, respectively) and have exhibited significant pharmacological effects in animal sleep studies. However, no selective dual activity H1/5-HT$_{2A}$ inverse agonists/antagonists are currently commercially available.

U.S. Pat. No. 4,192,803 describes certain substituted 4-(5H-pyrrolo[2,1-c][1,4]benzodiazepin-1'-yl)piperazinyl compounds for use as antipsychotics and neuroleptics.

The present invention provides a family of substituted (5H-pyrrolo[2,1-c][1,4]benzodiazepin-1'-yl)piperazin-1-yl]-2,2-dimethylpropanoic acid compounds with high inverse agonist potency for the H1 receptor and high antagonist potency for the 5-HT$_{2A}$ receptor. Certain compounds of the present invention are also selective for the H1 and 5-HT$_{2A}$ receptors, particularly as against other histamine receptors, serotonin receptors and other physiologically relevant receptors, particularly as against the 5-HT$_{2C}$ receptor, GABA$_A$ receptor, muscarinic receptors, dopaminergic receptors, adrenergic receptors, and the hERG channel. Certain compounds have also demonstrated through animal models that they may be useful for the treatment of sleep disorders characterized by poor sleep maintenance. As such, the compounds of the invention are believed to be useful for the treatment of sleep disorders characterized by poor sleep latency or poor sleep maintenance or both, such as the treatment of insomnia, as for example chronic or transient primary insomnia, or chronic or transient secondary insomnia, or both. Examples of secondary insomnia include, but are not limited to insomnia associated with depressive disorders (e.g. major depressive disorder, dysthymia, and/or cyclothymia), insomnia associated with anxiety disorders (e.g. generalized anxiety disorder and/or social phobia), insomnia associated with pain (e.g. fibromyalgia, chronic bone or joint pain, such as associated with inflammatory arthritis or osteoarthritis, or diabetic neuropathic pain), insomnia associated with allergic reactions (e.g. allergic asthma, pruritus, rhinitis, congestion, etc.), insomnia associated lung or airway disorders (e.g. with obstructive sleep apnea, reactive airway disease, etc.), insomnia associated with psychiatric disorders, dementia, and/or neurodegenerative diseases, and/or insomnia associated with circadian rhythm sleep disorders (e.g. shift work sleep disorder, jet lag disorder, delayed sleep phase disorder, advanced phase sleep disorder, and non-24 hour sleep-wake syndrome, etc.).

Further, certain of the compounds of the present invention demonstrate potentiation of their effects on non-rapid eye movement sleep (NREM sleep) and sleep maintenance when coadministered with selective serotonin reuptake inhibitors.

The present invention provides compounds of Formula I:

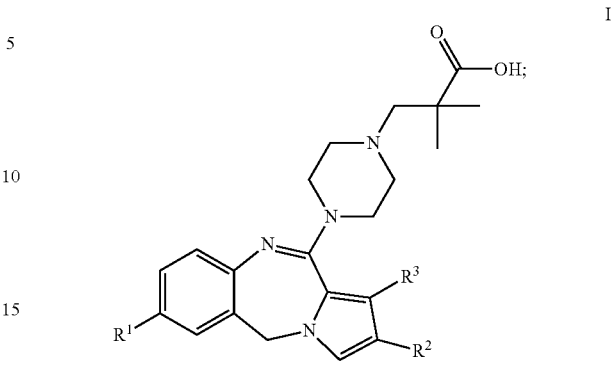

where R$^1$ is chloro or methyl;
R$^2$ is methyl, ethyl, isopropyl, chloro, bromo, trifluoromethyl, or methylthio; and
R$^3$ is hydrogen or methoxy;
or a pharmaceutically acceptable salt thereof.

In another aspect of the invention there is provided a pharmaceutical composition comprising a compound of Formula I or a pharmaceutically acceptable salt thereof, in combination with at least one pharmaceutically acceptable carrier, diluent, or excipient. Furthermore, this aspect of the invention provides a pharmaceutical composition adapted for the treatment of insomnia, as for example insomnia characterized by prolonged sleep latency or poor sleep maintenance or both, as for example primary insomnia, jet lag, shift work sleep disorder, delayed sleep phase disorder, advanced phase sleep disorder, and/or non-24 hour sleep-wake disorders, comprising a compound of Formula I or a pharmaceutically acceptable salt thereof, in combination with one or more pharmaceutically acceptable excipients, carriers, or diluents.

A further embodiment of this aspect of the invention provides a pharmaceutical composition comprising a compound according to Formula I, or pharmaceutically acceptable salt thereof, in combination with at least one pharmaceutically acceptable carrier, exciepient or diluent, and optionally other therapeutic ingredients. In a yet further embodiment of this aspect of the invention, the pharmaceutical composition further comprises a second therapeutic agent which is a serotonin reuptake inhibitor, as for example citalopram, paroxetine, fluoxetine and/or fluvoxetine.

The present invention also provides a method of treating insomnia, as for example insomnia characterized by prolonged sleep latency or poor sleep maintenance or both, as for example primary insomnia, jet lag, shift work sleep disorder, delayed sleep phase disorder, advanced phase sleep disorder, and/or non-24 hour sleep-wake disorders, in a mammal comprising administering to a mammal in need of such treatment an effective amount of a compound of Formula I or a pharmaceutically acceptable salt thereof. In another embodiment of this aspect of the invention, the method further comprises administering in simultaneous, separate or sequential combination, a second therapeutic agent which is a serotonin reuptake inhibitor, as for example citalopram, paroxetine, fluoxetine and/or fluvoxetine. In one particular embodiment of these methods of treatment, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of insomnia. In further embodiments, the insomnia is characterized by prolonged sleep latency or poor sleep maintenance or both, as for example primary insomnia, jet lag, shift work sleep disorder, delayed sleep phase disorder, advanced phase sleep disorder, and/or non-24 hour sleep-wake disorders. In another embodiment of this aspect, the invention provides a compound according to Formula I, or a pharmaceutically acceptable salt thereof, for use in simultaneous, separate or sequential combination with a serotonin reuptake inhibitor, as for example citalopram, paroxetine, fluoxetine and/or fluvoxetine, in the treatment of insomnia. One particular embodiment of this aspect of the inventions, the uses are in mammals, particular humans.

Another aspect of this invention provides the use of a compound of Formula I, or a pharmaceutically acceptable salt thereof, in the manufacture of a medicament for the treatment of insomnia, as for example primary insomnia characterized by prolonged sleep latency or poor sleep maintenance or both, as for example primary insomnia, jet lag, shift work sleep disorder, delayed sleep phase disorder, advanced phase sleep disorder, and/or non-24 hour sleep-wake disorders. Another embodiment of this aspect of the invention provides the use of a compound of Formula I, or a pharmaceutically acceptable salt thereof, and a second therapeutic agent which is a serotonin reuptake inhibitor, as for example citalopram, paroxetine, fluoxetine and/or fluvoxetine, in the manufacture of a medicament for the treatment of insomnia, as for example, insomnia characterized by prolonged sleep latency and/or poor sleep maintenance, as for example primary insomnia, jet lag, shift work sleep disorder, delayed sleep phase disorder, advanced phase sleep disorder, and/or non-24 hour sleep-wake disorders.

For clarity, the following numbering of the tricyclic ring structure will be used throughout the application:

Compounds of this invention have basic and acidic moieties, and accordingly react with a number of organic and inorganic acids and bases to form pharmaceutically acceptable salts. Pharmaceutically acceptable salts of each of the compounds of the present invention are contemplated within the scope of the present application. The term "pharmaceutically acceptable salt" as used herein, refers to any salt of a compound of the invention that is substantially non-toxic to living organisms. Such salts include those listed in *Journal of Pharmaceutical Science*, 66, 2-19 (1977), which are known to the skilled artisan.

Preferred classes of compounds of the present invention are compounds wherein:
1) $R^3$ is hydrogen;
2) $R^3$ is methoxy;
3) $R^1$ is chloro;
4) $R^1$ is methyl;
5) $R^1$ is chloro and $R^3$ is hydrogen;
6) $R^1$ is methyl and $R^3$ is hydrogen;
7) $R^2$ is methyl, ethyl, or isopropyl;
8) $R^2$ is methyl;
9) $R^2$ is chloro or bromo;
10) $R^2$ is chloro;
11) $R^2$ is trifluoromethyl; and
12) $R^2$ is methylthio.

It will be understood that further preferred compounds are those combining the above preferred selections for a given substituent or substituents with preferred selections of other substituents. Examples of such combinations include, but are not limited to the following preferred classes of compounds:
13) preferred compounds of any one of preferred classes 7-12 (which are preferred selections for $R^2$) wherein $R^3$ is hydrogen (preferred class 1);
14) preferred compounds of any one of preferred classes 7-12 (which are preferred selections for $R^2$) wherein $R^1$ is chloro and $R^3$ is hydrogen (preferred class 5); and
15) preferred compounds of preferred class 8 wherein $R^3$ is methoxy (preferred class 2).

Specific preferred compounds are those described in the Examples including their freebases and pharmaceutically acceptable salts thereof.

One certain preferred compound is
3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof (i.e. the compound of Example 1 and pharmaceutically acceptable salts thereof).

Abbreviations used herein are defined as follows:
"BSA" means bovine serum albumin.
"DCG IV" means (2S,2'R,3'R)-2-(2',3'-dicarboxycyclopropyl)glycine.
"DCM" means dichloromethane.
"DMEM means Dulbecco's Minimum Eagle's Medium.
"DMSO" means dimethyl sulfoxide.
"DPBS" means Dulbecco's Phosphate Buffered Saline.
"DSC" means differential scanning calorimetry.
"EtOAc" means ethyl acetate.
"GC" means gas chromatography.
"HBSS" means Hank's Buffered Salt Solution.
"HEPES" means 4-(2-hydroxyethyl)-1-piperazine ethanesulfonic acid.
"HPLC" means high pressure liquid chromatography.
"hr." or "h" means hour or hours.
"IBMX" means 3-isobutyl-1-methylxanthine
"$IC_{50}$" means the concentration at which 50% of the maximum inhibition is achieved.
"i.v." means intravenous or intravenously.
"i.p." means intraperitoneal.
"LC-MS" means HPLC-mass spectrography.
"MeOH" means methanol.
"mFST" means mouse forced swim test; an animal model for antidepressant activity.
"min." or "m" means minutes.
"mp" means melting point.
"MS" means mass spectroscopy.
"MS (ES+)" means mass spectroscopy using electrospray ionization.
"MTBE" means methyl t-butyl ether.
"NMR" means nuclear magnetic resonance.
"p.o." means per os, by mouth.
"SCX-2" means Biotage Isolute Flash SCX-2® strong cation exchange columns.
"THF" means tetrahydrofuran.

General Chemistry

The compounds of the present invention can be prepared according to the following synthetic schemes by general methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Generally, a compound of formula I may be prepared from a compound of formula II where Pg is a suitable carboxyl protecting group (Scheme 1). More specifically, a compound of formula II where Pg is a $C_1$-$C_3$ alkyl group is reacted with a suitable deprotection agent such as aqueous sodium hydroxide in an organic co-solvent such isopropyl alcohol to provide, following neutralization with an acid, a compound of formula I.

Scheme 1

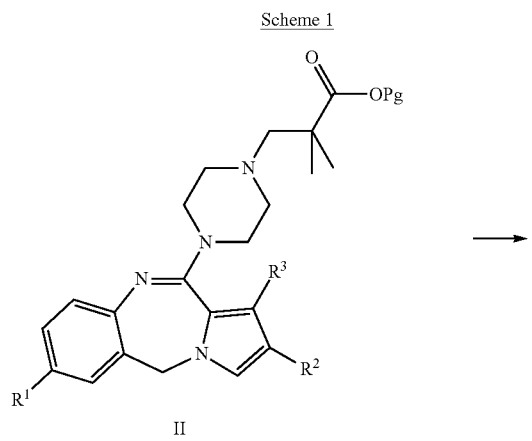

II

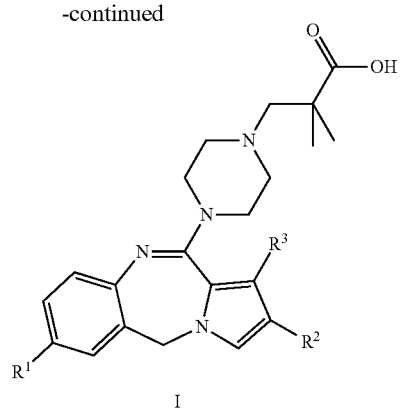

I

Generally, a compound of formula II may be prepared from a compound of formula III or a compound of formula IV (Scheme 2). More specifically, a compound of formula III is reacted with phosphoryl chloride in a suitable solvent such as methoxybenzene or dichloromethane to provide the imino chloride intermediate. The imino chloride may be isolated or reacted directly with Pg-2,2-dimethyl-3-piperazin-1-yl propanoate in the presence of a suitable base such as potassium carbonate to provide a compound of formula II. The reaction is carried out in a suitable solvent such as acetonitrile. Alternatively, the imino chloride may be reacted with piperazine in the presence of a suitable base such as cesium carbonate to provide a compound of formula IV. The reaction is carried out in a suitable solvent such as acetonitrile. A compound of formula IV is alkylated with Pg-2,2-dimethyl-3-oxopropanoate in the presence of a suitable reducing agent such as sodium triacetoxyborohydride to provide a compound of formula II. The reaction is typically carried out in a solvent such as dichloromethane.

Scheme 2

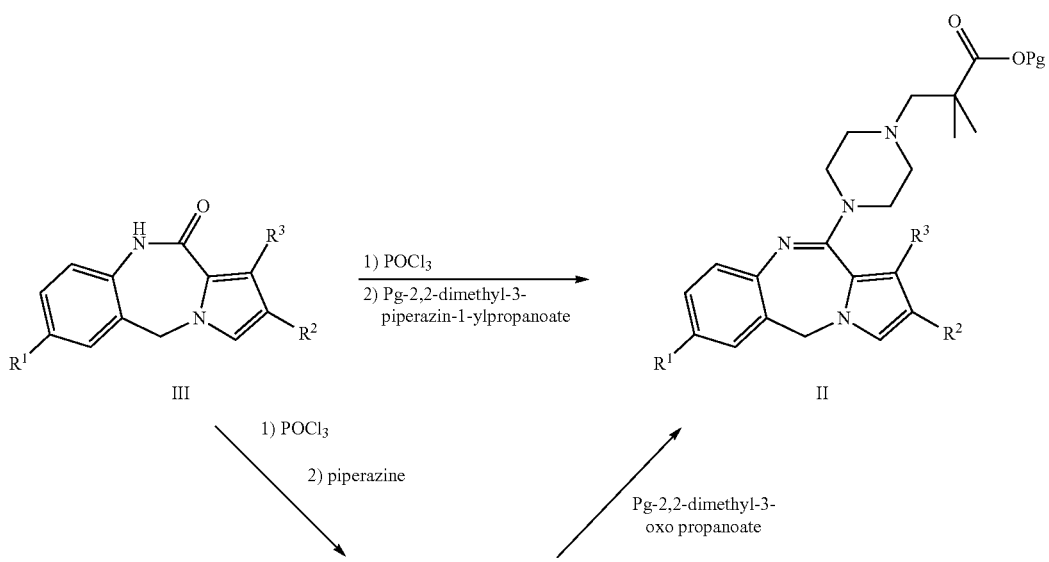

-continued

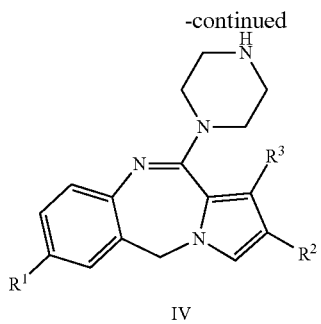

IV

A compound of formula III may be prepared from a compound of formula V where $R^4$ is methyl or ethyl (Scheme 3). More specifically, a compound of formula V is reacted with an agent suitable for reducing the aryl nitro group to the corresponding aniline. Suitable reducing agents include hydrogen in the presence of a transition metal catalyst such as platinum; iron in acetic acid; and tin dichloride in hydrochloric acid. The corresponding aniline may be first isolated or directly reacted under cyclization conditions to provide a compound of formula III. The cyclization is carried out in the presence of an acid such as hydrochloric acid or a base such as potassium t-butoxide. A compound of formula V where $R^4$ is methyl or ethyl may be prepared as described in the preparations or by procedures known in the chemical arts for the production of structurally analogous compounds.

Scheme 3

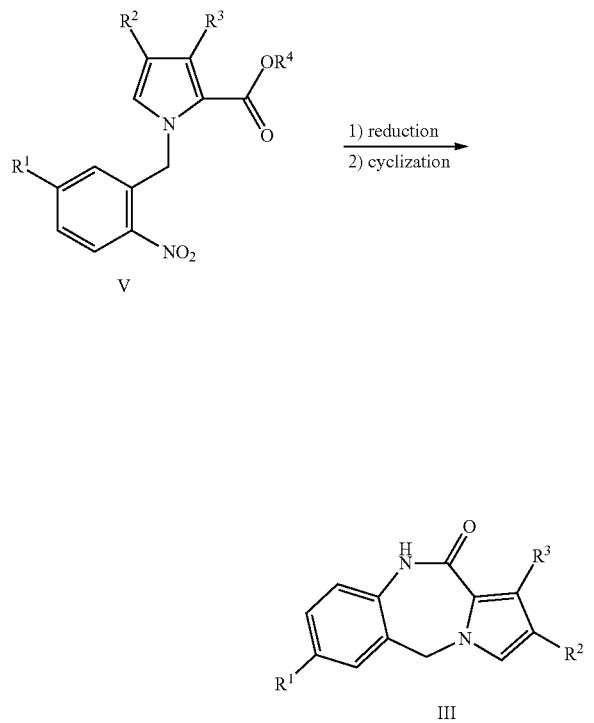

In the following illustrative preparations and examples, reagents were obtained from a variety of commercial sources. Solvents are generally removed under reduced pressure (evaporated). In some procedures indicated yields are representative crude yields for products which are isolated by evaporation or filtration and used directly without further purification.

PREPARATION 1

Synthesis of methyl 2,2-dimethyl-3-oxo-propanoate

Add methyl 3-hydroxy-2,2-dimethylpropanoate (33 g, 250 mmol) to Dess-Martin periodinane (106 g, 250 mmol) suspended in DCM (1000 mL) at 0° C. and stir at room temperature for 18 h. Filter the reaction mixture through a celite bed and concentrate the filtrate. Wash the concentrated filtrate with pentane (2×200 mL). Separate the pentane layer and concentrate in vacuo to give methyl 2,2-dimethyl-3-oxo-propanoate (31.93 g, quantitative). $^1$H NMR ($d_6$-DMSO) δ 9.59 (s, 1H), 3.67 (s, 3H), 1.26 (s, 6H).

PREPARATION 2

Synthesis of tert-butyl 4-(3-methoxy-2,2-dimethyl-3-oxopropyl)piperazine-1-carboxylate

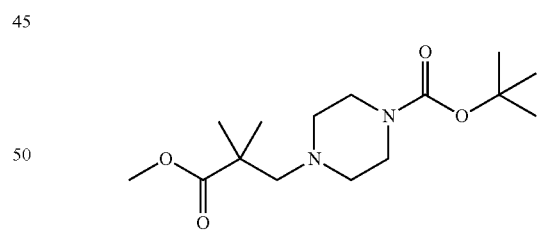

Stir a solution of methyl 2,2-dimethyl-3-oxo-propanoate (30.88 g, 237.31 mmoles) and tert-butyl piperazine-1-carboxylate (34.00 g, 182.55 mmoles) in DCM (500 mL) at room temperature for 20 minutes. Add acetic acid (2 equiv); 20.92 mL, 365.09 mmoles) followed by sodium triacetoxyborohydride (1.4 equiv; 54.17 g, 255.56 mmoles) over 0.5 h and stir the resulting mixture stirred at room temperature overnight. Carefully quench with water (250 mL) and transfer the mixture to a separating funnel with DCM (300 mL). Wash the resulting organic layer with brine. Dry over $MgSO_4$, filter and evaporate to give tert-butyl 4-(3-methoxy-2,2-dimethyl-3-oxopropyl)piperazine-1-carboxylate. (58 g, 100%). MS (m/z): 301.2 (M+1).

PREPARATION 3

Synthesis of methyl 2,2-dimethyl-3-(piperazin-1-yl)propanoate dihydrochloride

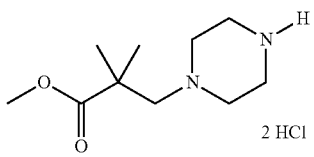

2 HCl

To a solution of tert-butyl 4-(3-methoxy-2,2-dimethyl-3-oxopropyl)piperazine-1-carboxylate (58.0 g, 193.08 mmoles) in isopropyl alcohol (150 mL) add a 4M dioxane solution of hydrogen chloride ((4 equiv); 193.08 mL, 772.31 mmoles) over 15 minutes, observing gas evolution and a fine precipitate. Heat at 55° C. for 3 h to give a white precipitate. Cool to 10° C. and collect the white solid by filtration, wash with further isopropyl alcohol (30 mL), then EtOAc. Dry in a vacuum oven at 45° C. for 1 h to give methyl 2,2-dimethyl-3-(piperazin-1-yl)propanoate dihydrochloride (31 g, 59% yield). MS (m/z): =201.1 (M+1).

PREPARATION 4

Synthesis of methyl 2,2-dimethyl-3-(piperazin-1-yl)propanoate hydrochloride

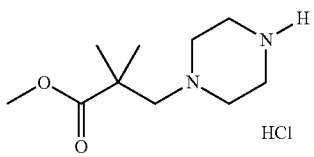

HCl

Dissolve methyl 2,2-dimethyl-3-(piperazin-1-yl)propanoate dihydrochloride (112.0 g, 409.95 mmoles) in water (250 mL). Add solid sodium bicarbonate to give an aqueous layer of pH 4 and extract the mixture into a solution of 10% DCM in diethyl ether (300 mL) to remove some dark solid matter and some color. Discard the organic layer. Basify the aqueous phase to pH 8 with 2M aqueous sodium hydroxide solution, then saturate with solid sodium chloride. Extract into a 10% solution of isopropanol in chloroform. Add further 2M aqueous sodium hydroxide to maintain pH 8. Repeat the extraction into a 10% solution of isopropanol in chloroform. Continue the extraction process until 85% of the expected material has been recovered. Wash the isopropanol in chloroform solution with brine, dry over $Na_2SO_4$, filter and evaporate to give methyl 2,2-dimethyl-3-(piperazin-1-yl)propanoate hydrochloride (82.1 g % yield). MS (m/z): 201.1 (M+1).

PREPARATION 5

Synthesis of methyl 4-ethenyl-1H-pyrrole-2-carboxylate

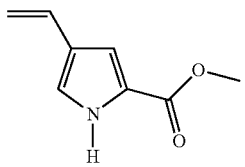

Degas, by purging with nitrogen for 10 minutes, a solution of methyl 4-bromo-1H-pyrrole-2-carboxylate (2.0 g, 9.8 mmoles), triethenylboroxin pyridine (1.3 equiv; 3.1 g, 12.7 mmoles), and potassium carbonate (3 equiv; 4.1 g, 29.4 mmoles) in a mixture of 1,4-dioxane (20 mL) and water (10 mL). Add tris(dibenzylideneacetonyl)bis-palladium ($Pd_2(dba)_3$) (0.01 equiv; 0.0925 g, 98.0 µmoles) and 1,1'-bis(di-tert-butylphosphino)ferrocene (dtbpf) (0.03 equiv; 0.0853 g, 294.1 µmoles) and heat at 95° C. for 3 h. Cool to room temperature then partition between water (50 mL) and a 1:1 mixture of hexanes/diethyl ether (100 mL). The organic layer is washed with water (2×50 mL) then brine. Dry over $Na_2SO_4$, filter and evaporate to give methyl 4-ethenyl-1H-pyrrole-2-carboxylate as a straw colored oil (1.5 g). Use without further purification. 1H-NMR ($CDCl_3$), δ: 8.90 (1H, br. s), 7.02 (1H, m), 6.95 (1H, m), 6.56 (1H, q) 5.48 (1H, dd), 5.05 (1H, dd), 3.86 (3H, s).

PREPARATION 6

Synthesis of methyl 4-ethyl-1H-pyrrole-2-carboxylate

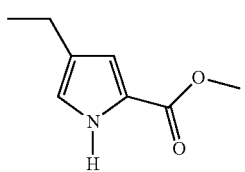

Charge to a 500 mL Parr bottle, a mixture of 5% palladium on charcoal (0.2 g) in ethanol (25 mL) and add methyl 4-ethenyl-1H-pyrrole-2-carboxylate (1.4 g, 9.3 mmoles). Hydrogenate at 206.8 kPa for 3 h to give complete conversion by LC-MS. Filter through celite and evaporate to give an oil. Pass through a silica gel pad with iso-hexane/ethyl acetate (100:0 to 75:25) to give the title compound as a pale yellow oil (1.12 g). $^1$H-NMR (CDCl$_3$), δ: 8.87 (1H, br. s), 6.73-6.78 (2H, m), 3.83 (3H, s), 2.50 (2H, q, J=7.8 Hz) and 1.19 (3H, t, J=7.3 Hz).

PREPARATION 7

Synthesis of methyl 4-(prop-1-en-2-yl)-1H-pyrrole-2-carboxylate

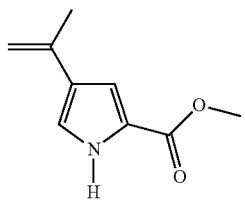

Mix methyl 4-iodo-1H-pyrrole-2-carboxylate (1.5 g, 5.98 mmoles), 4,4,5,5-tetramethyl-2-(prop-1-en-2-yl)-1,3,2-dioxaborolane (3.01 g, 17.98 mmoles) 1,1'-bis(di-tert-butylphosphino)ferrocene (dtbpf) (0.3 g, 0.06 mmoles), tris (dibenzylideneacetonyl)bis-palladium (Pd$_2$(dba)$_3$) (0.3 g, 0.06 mmoles), tripotassium phosphate (2.54 g, 11.95 mmoles) and methanol (12 mL). Heat the mixture in a sealed tube in a microwave at 140° C. for 30 minutes. Cool, filter the reaction mixture and wash sinter with methanol, evaporate the filtrate under reduced pressure and chromatograph on silica eluting with isohexane/dichloromethane (gradient elution, 100:0 to 0:100). Evaporate the fractions containing product to give methyl 4-(prop-1-en-2-yl)-1H-pyrrole-2-carboxylate. (0.679 g, 68.79% yield). MS (m/z): 166.1 (M+1).

PREPARATION 8

Synthesis of ethyl 3-methoxy-4-methyl-1H-pyrrole-2-carboxylate

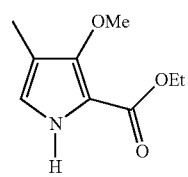

Add dimethyl sulfate (3 mL, 3.99 g, 31.63 mmoles) to a mixture of 3-hydroxy-4-methyl-1H-pyrrole-2-carboxylic acid ethyl ester (3.5 g, 20.69 mmoles) and 2M sodium hydroxide (75 mL, 1500 mmoles) and stir the reaction mixture vigorously for 30 mins at room temp (water cooling bath applied). Collect the resultant precipitate and wash with water. Add more dimethyl sulfate (3 mL, 3.99 g, 31.63 mmoles) to the filtrate and stir for 30 minutes. Collect the resultant precipitate and wash with water. Add more dimethyl sulfate (3 mL, 3.99 g, 31.63 mmoles) to the filtrate and stir for 1 h. Combine the isolated precipitates and dry in a vacuum oven at 50° C. for 30 minutes to give ethyl 3-methoxy-4-methyl-1H-pyrrole-2-carboxylate (3.221 g, 84.98% yield). MS (m/z): 184.09 (M+1).

PREPARATION 9

Synthesis of ethyl 1-(5-chloro-2-nitrobenzyl)-4-methyl-1H-pyrrole-2-carboxylate

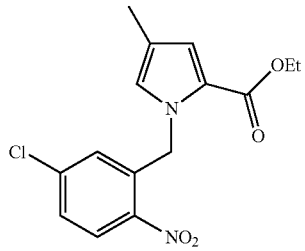

Vigorously stir a solution of 2-(bromomethyl)-4-chloro-1-nitro-benzene (25.02 g, 99.88 mmoles) in DCM (200 mL), and to this add a solution of ethyl 4-methyl-1H-pyrrole-2-carboxylate (15 g, 97.92 mmoles) in DCM (200 mL). Then add 30-hydrated tetra-n-butylammonium hydroxide (0.508 g) and cool the stirred mixture under nitrogen to 5° C. using an external ice-bath. Add 25% aq. sodium hydroxide (200 mL) dropwise over 15 minutes observing the internal temperature rise to 10° C. Stir and allow to warm to room temperature. Stir at room temperature for 3.5 h. Add further 50% aq. sodium hydroxide (20 mL) and stir at room temperature for a further 1 h. Stop the stirring and allow the layers to separate. Transfer to a separating funnel and wash the organic layer with 1N hydrochloric acid (200 mL), observing the pH of this layer to be acidic using indicator paper. Next wash the organic layer with water (600 mL) and then brine (600 mL) and finally dry over Na$_2$SO$_4$. Filter the mixture and remove the solvent in vacuo at 40° C. to give an orange oil. Purify by passing through a silica gel pad with iso-hexane/ethyl acetate (gradient eluting from 10 to 20%) to give ethyl 1-(5-chloro-2-nitrobenzyl)-4-methyl-1H-pyrrole-2-carboxylate as a yellow oil (33 g, quantitative). MS (m/z): 322.98 (M+1).

PREPARATION 9 alternative

Synthesis of ethyl 1-(5-chloro-2-nitrobenzyl)-4-methyl-1H-pyrrole-2-carboxylate

Under a nitrogen atmosphere with stirring add cesium carbonate (96 g, 295 mmoles) to a solution of ethyl 4-methyl-1H-pyrrole-2-carboxylate (30 g, 196 mmoles) in DMF (240 mL) and heat the reaction mixture to 40° C. to 45° C. for 1 hour. Cool the reaction mixture to room temperature and add a solution of 2-(bromomethyl)-4-chloro-1-nitro-benzene (54 g, 216 mmoles) in DMF (120 mL) drop-wise. Stir the resulting suspension for 1.5 h to 2.0 h, filter the solids and rinse the filtercake with DMF (45 mL). Transfer the solids to a clean reaction vessel, add water (200 mL) and cool the suspension to 10° C. to 15° C. with stirring for 1 h to 2 h. Filter the suspension, rinse with water (75 mL) and transfer the solids to another reaction vessel. Add ethanol (125 mL) and stir the suspension at 5° C. to 10° C. for 1 h to 2 h. Filter the solids, rinse the filtercake with ethanol (20 mL), and dry the solids in an oven at less than 50° C. under reduced pressure to give ethyl 1-(5-chloro-2-nitrobenzyl)-4-methyl-1H-pyrrole-2-carboxylate as a yellow solid (54 g, 94.1% purity, 73.3% yield).

PREPARATION 10

Synthesis of ethyl 4-bromo-1-(5-chloro-2-nitrobenzyl)-1H-pyrrole-2-carboxylate

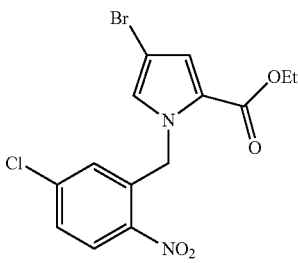

Wash 60% mineral oil suspended sodium hydride (1.2 equiv; 1.1 g, 27.52 mmoles) with a small amount of isohexane (×2). Suspend in N,N-dimethylacetamide (15 mL) and chill in an ice-bath. Add ethyl 4-bromo-1H-pyrrole-2-carboxylate (5.0 g, 22.93 mmoles) portionwise over 15 minutes allowing gas evolution to subside between additions. Stir at room temperature for 15 minutes to give a brown solution. Add 2-(bromomethyl)-4-chloro-1-nitro-benzene (1.15 equiv; 6.61 g, 26.37 mmoles) in portions over 15 minutes and stir the resulting purple solution at room temperature for 2.5 h. Cool in an ice-bath and quench with water (10 mL). Partition between 1M hydrochloric acid (100 mL) and EtOAc (300 mL). Wash the organic layer with water (2×100 mL) then brine. Dry over $Na_2SO_4$ and decolorize with activated charcoal. Filter through celite and evaporate to give ethyl 4-bromo-1-(5-chloro-2-nitrobenzyl)-1H-pyrrole-2-carboxylate as a an orange oil (9.1 g, quantitative). $^1$H-NMR ($CDCl_3$) δ: 8.12 (1H, d), 7.40 (1H, dd), 7.07 (1H, d), 6.92 (1H, d), 6.53 (1H, d), 5.87 (2H, s), 4.17 (2H, q), 1.25 (3H, t).

The following compounds are prepared essentially by the method of Preparation 10.

| Preparation No. | Name | Structure | Physical Data |
|---|---|---|---|
| 11 | Ethyl 4-methyl-1-(5-methyl-2-nitrobenzyl)-1H-pyrrole-2-carboxylate | 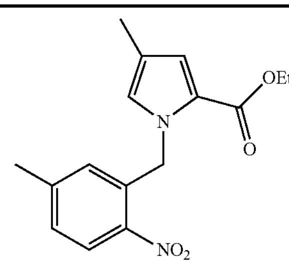 | MS (m/z): 303.09 (M + 1). |
| 12 | Ethyl 1-(5-methyl-2-nitrobenzyl)-4-(trifluoromethyl)-1H-pyrrole-2-carboxylate | 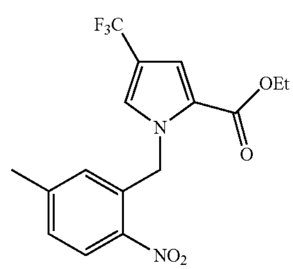 | 1H NMR (d6-DMSO) δ: 8.06 (1H, d), 7.90 (1H, s), 7.37 (1H, d), 7.25 (1H, s), 6.31 (1H, s), 5.87 (2H, s), 4.09 (2H, q), 2.27 (3H, s), 1.13 (3H, t) |
| 13 | Methyl 4-chloro-1-(5-chloro-2-nitrobenzyl)-1H-pyrrole-2-carboxylate | 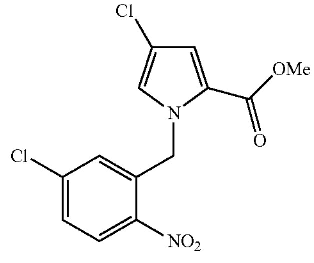 | 1H NMR (CDCl3) δ: 8.16 (1H, d), 7.40 (1H, dd), 6.98 (1H, d), 6.88 (1H, d), 6.53 (1H, d), 5.86 (2H, s), 3.73 (3H, s) |

-continued

| Preparation No. | Name | Structure | Physical Data |
|---|---|---|---|
| 14 | Methyl 1-(5-chloro-2-nitrobenzyl)-4-(methylsulfanyl)-1H-pyrrole-2-carboxylate | 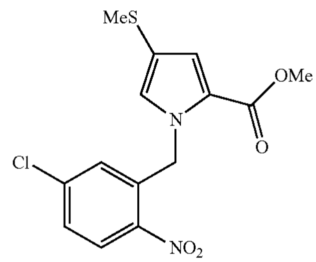 | MS (m/z): 340.98 (M + 1) |
| 15 | Methyl 4-bromo-1-(5-methyl-2-nitrobenzyl)-1H-pyrrole-2-carboxylate | 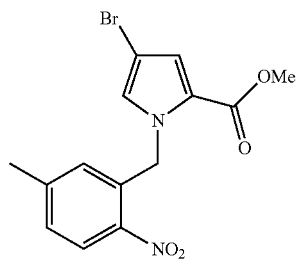 | MS (m/z): 352.98 (M + 1) |
| 16 | Methyl 1-(5-chloro-2-nitrobenzyl)-4-ethyl-1H-pyrrole-2-carboxylate | 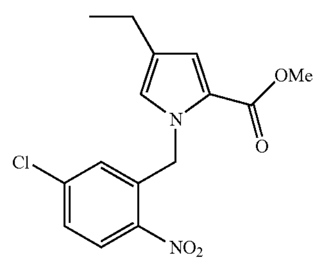 | MS (m/z): 323.18 (M + 1) |
| 17 | Methyl 1-(5-chloro-2-nitrobenzyl)-4-(prop-1-en-2-yl)-1H-pyrrole-2-carboxylate | 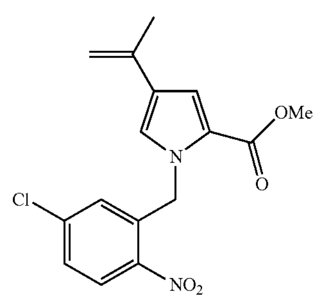 | MS (m/z): 334.98 (M + 1) |
| 18 | Ethyl 1-(5-chloro-2-nitrobenzyl)-4-(trifluoromethyl)-1H-pyrrole-2-carboxylate | 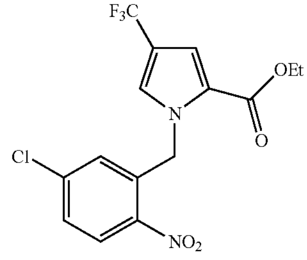 | 1H NMR (CDCl3) d: 8.14 (1H, d), 7.42 (1H, dd), 7.25 (1H, s), 7.22 (1H, d), 6.51 (1H, d), 5.92 (2H, s), 4.20 (2H, q), 1.28 (3H, t). |

| Preparation No. | Name | Structure | Physical Data |
|---|---|---|---|
| 19 | Methyl 1-(5-methyl-2-nitrobenzyl)-4-(methylsulfanyl)-1H-pyrrole-2-carboxylate | 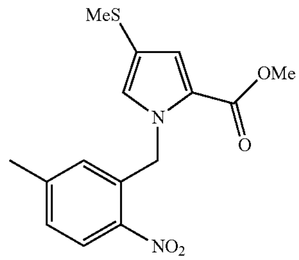 | MS (m/z): 321.03 (M + 1) |
| 20 | Ethyl 1-(5-chloro-2-nitrobenzyl)-3-methoxy-4-methyl-1H-pyrrole-2-carboxylate | 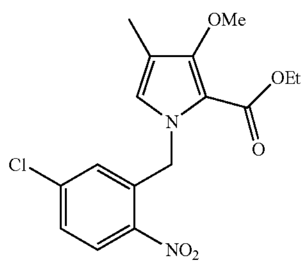 | MS (m/z): 353.13 (M + 1) |
| 21 | Ethyl 3-methoxy-4-methyl-1-(5-methyl-2-nitrobenzyl)-1H-pyrrole-2-carboxylate | 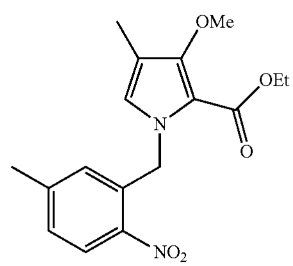 | MS (m/z): 333.18 (M + 1) |

PREPARATION 22

Synthesis of ethyl 1-(2-amino-5-chlorobenzyl)-4-methyl-1H-pyrrole-2-carboxylate

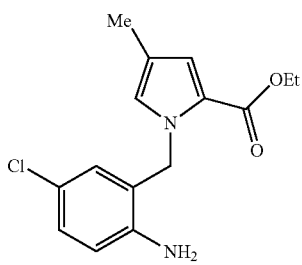

Charge 5% platinum(S)/charcoal (2.5 g), and ethyl 1-(5-chloro-2-nitrobenzyl)-4-methyl-1H-pyrrole-2-carboxylate (16.0 g, 49.57 mmoles) to a 500 mL Parr bottle. Add ethanol (200 mL) then zinc dibromide (0.22 equiv; 2.46 g, 10.91 mmoles) and place the mixture under hydrogen at 275.8 kPa and hydrogenate at room temperature overnight, monitoring formation of a partially hydrogenated intermediate. Remove the Parr bottle, heat gently in a water bath to dissolve the crystallized material, and filter through celite. Combine with the filtrate from an identical run and evaporate to give ethyl 1-(2-amino-5-chlorobenzyl)-4-methyl-1H-pyrrole-2-carboxylate an off-white solid. Place under high vacuum to remove residual ethanol to give the material (35 g, quantitative). MS (m/z): 293.1 (M+1).

PREPARATION 22 ALTERNATIVE

Synthesis of ethyl 1-(2-amino-5-chlorobenzyl)-4-methyl-1H-pyrrole-2-carboxylate

In a reaction vessel under nitrogen charge a solution of ethyl 1-(5-chloro-2-nitrobenzyl)-4-methyl-1H-pyrrole-2-carboxylate (100.0 g, 310 mmoles) in THF (800 mL) and add zinc dibromide (0.22 equiv; 15.4 g, 68.4 mmoles) with stirring at room temperature. Charge a slurry of 5% platinum(S)/charcoal (13.3 g) in THF (25 mL), and place the vessel under hydrogen at 380 kPa. Hydrogenate at room temperature for 30 hr. to 40 hr., monitoring formation of a partially hydrogenated intermediate and filter over diatomite. Rinse the filter aid with THF (300 mL) and concentrate the filtrate, at below 40° C., to arrive at a volume of approximately 200 mL. Add DCM (250 mL), concentrate the solution, at below 40° C., to arrive at a volume of approximately 200 mL, and add additional DCM (600 mL). This process can be repeated as necessary to remove undesired levels of THF from the reaction mixture. Charge water (500 mL), separate the layers, and wash the organic layer with water (300 mL), followed by 25% aqueous solution of sodium chloride (250 mL). Concentrate the solution, 40° C., to arrive at a volume of approximately 200 mL, add heptane (400 mL), and concentrate the solution, at below 40° C., to arrive at a volume of approximately 200 mL. Add heptane (400 mL) and heat the reaction mixture to 40-45° C. with stirring for 2-3 hr. Cool the reaction mixture to 5-10° C. and continue stirring at this temperature for 1-2 hr. Filter the resulting solids and dry in an oven at less than 50° C. under reduced pressure to give ethyl 1-(2-amino-5-chlorobenzyl)-4-methyl-1H-pyrrole-2-carboxylate (81.4 g, 95.8% purity, 85.9% yield) as a yellow solid.

The following compounds are prepared essentially by the method of Preparation 22.

PREPARATION 26

Synthesis of ethyl 1-(2-amino-5-chlorobenzyl)-4-bromo-1H-pyrrole-2-carboxylate

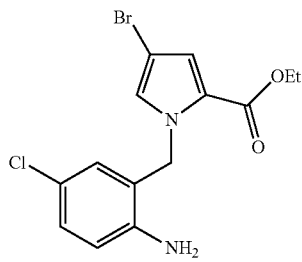

To a well-stirred solution of ethyl 4-bromo-1-(5-chloro-2-nitrobenzyl)-1H-pyrrole-2-carboxylate (9.1 g, 23.48 mmoles) in acetic acid (60.00 mL) at 70° C., add iron (5

| Preparation No. | Name | Structure | MS (m/z): (M + 1). |
|---|---|---|---|
| 23 | Ethyl 1-(2-amino-5-methylbenzyl)-4-methyl-1H-pyrrole-2-carboxylate | 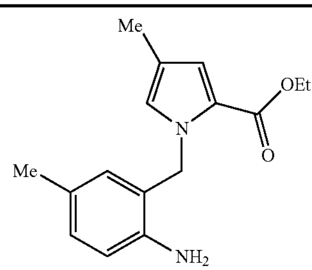 | 273.09 |
| 24 | Ethyl 1-(2-amino-5-methylbenzyl)-4-(trifluoromethyl)-1H-pyrrole-2-carboxylate | 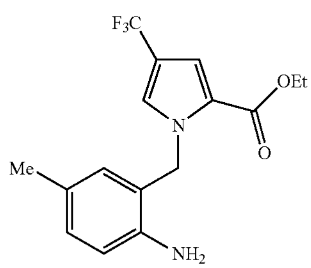 | 327.18 |
| 25 | Ethyl 1-(2-amino-5-methylbenzyl)-3-methoxy-4-methyl-1H-pyrrole-2-carboxylate | | 303.19 | equiv; 6.56 g, 117.38 mmoles) in portions over 0.5 h. Halfway through the addition, observe an exotherm to maintain a temperature of 85° C. with the oil-bath removed. The reaction mixture will get thicker as the exotherm dissipates and the rest of the iron can be added. Stir at 85° C. for 0.5 h. Cool to room temperature and pour onto water (200 mL). Extract into chloroform (2×200 mL). Combine organic layers and wash with water (2×100 mL) then saturated aqueous $NaHCO_3$ solution. Dry over $Na_2SO_4$, filter and evaporate to the title compound as an orange oil (7.7 g, 92% yield). MS (m/z): 358.98 (M+1).

The following compounds are prepared essentially by the method of Preparation 26.

| Preparation No. | Name | Structure | MS (m/z): (M + 1). |
|---|---|---|---|
| 27 | Methyl 1-(2-amino-5-chlorobenzyl)-4-chloro-1H-pyrrole-2-carboxylate | 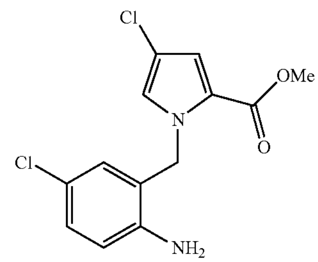 | 298.99/ 301.09 |
| 28 | Methyl 1-(2-amino-5-chlorobenzyl)-4-(methylsulfanyl)-1H-pyrrole-2-carboxylate | 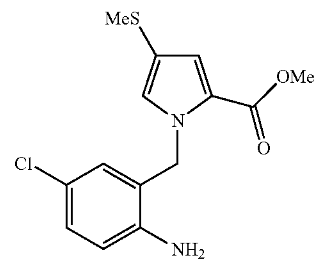 | 311.13 |
| 29 | Methyl 1-(2-amino-5-methylbenzyl)-4-bromo-1H-pyrrole-2-carboxylate | 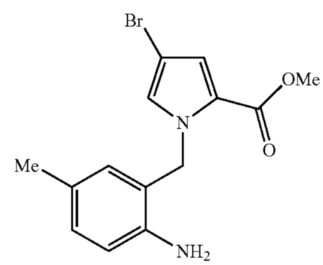 | 322.98 |
| 30 | Methyl 1-(2-amino-5-chlorobenzyl)-4-ethyl-1H-pyrrole-2-carboxylate | 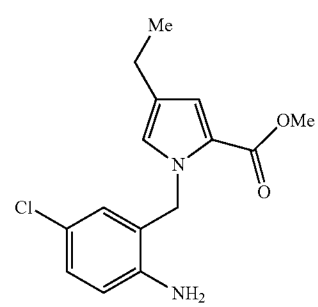 | 293.14 |
| 31 | Methyl 1-(2-amino-5-chlorobenzyl)-4-(propan-2-yl)-1H-pyrrole-2-carboxylate | 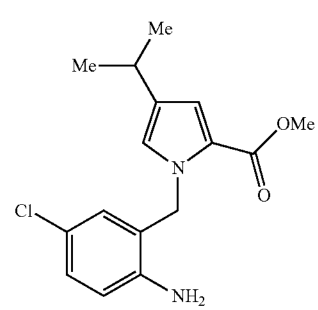 | 307.09 |

PREPARATION 32

Synthesis of 7-chloro-2-methyl-5,10-dihydro-11H-pyrrolo[2,1-c][1,4]benzodiazepin-11-one

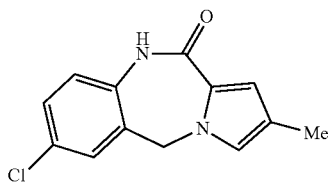

To a solution of ethyl 1-[(2-amino-5-chloro-phenyl)methyl]-4-methyl-pyrrole-2-carboxylate (35 g, 119.55 mmoles) in dimethyl sulfoxide (120 mL) add potassium t-butoxide (14.76 g, 131.5 mmoles) over 10 minutes. Heat at 80° C. (oil-bath temperature) for 1 h. Allow to cool then pour onto water (400 mL). Collect the resulting brown powdery solid by filtration, washing well with water. Suck as dry as possible on the sinter then transfer to a dish and dry in a vacuum oven at 55° C. over phosphorus pentoxide overnight, to give 7-chloro-2-methyl-5,10-dihydro-11H-pyrrolo[2,1-c][1,4]benzodiazepin-11-one (22 g, 91%). MS (m/z): 247.1 (M+1).

PREPARATION 32 ALTERNATIVE

Synthesis of 7-chloro-2-methyl-5,10-dihydro-11H-pyrrolo[2,1-c][1,4]benzodiazepin-11-one To a solution of ethyl 1-[(2-amino-5-chloro-phenyl)methyl]-4-methyl-pyrrole-2-carboxylate (20 g, 68.3 mmoles) in dimethyl sulfoxide (60 mL) add potassium t-butoxide (8.4 g, 74.9 mmoles) in DMSO (40 mL) and heat the reaction mixture to 75-80° C. for 1-2 hr. Add water (200 mL) slowly, cool to room temperature, and stir for 1-2 hr. Filter the solids, wash the filtercake with water (75 mL), and transfer the solids to a clean reaction vessel. Add THF (100 mL) and heat the reaction mixture to 30-35° C. until the solids dissolve. Add DCM (350 mL) and continue to stir at 30-35° C. for 1-2 hr. Add 1N hydrochloric acid (250 mL) and continue to stir at 30-35° C. for 1-2 hr. Separate the layers, wash the organic layer with 1N hydrochloric acid (250 mL) followed by a 25% aqueous solution of sodium chloride (50 mL), and concentrate the solution, at below 50° C., to arrive at a volume of approximately 25 mL. Add ethanol (50 mL), concentrate the solution, at below 50° C., to arrive at a volume of approximately 25 mL, and add additional ethanol (50 mL). Concentrate the solution, at below 50° C., to arrive at a volume of approximately 25 mL, heat the reaction mixture to 45-50° C., and stir for 1-2 hr. Cool the reaction mixture to 5-10° C. with stirring for 2-3 hr., and filter the resulting solids. Rinse the filtercake with ethanol (25 mL) and dry in an oven at less than 50° C. under reduced pressure to give 7-chloro-2-methyl-5,10-dihydro-11H-pyrrolo[2,1-c][1,4]benzodiazepin-11-one as an off-white solid (14.9 g, 99.9% purity, 88.5% yield).

The following compounds are prepared essentially by the method of Preparation 32.

| Preparation No. | Name | Structure | MS (m/z): (M + 1). |
|---|---|---|---|
| 33 | 2,7-Dimethyl-5,10-dihydro-11H-pyrrolo[2,1-c][1,4]benzodiazepin-11-one | 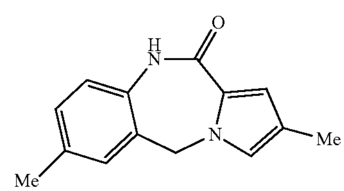 | 227.09 |
| 34 | 2-Bromo-7-chloro-5,10-dihydro-11H-pyrrolo[2,1-c][1,4]benzodiazepin-11-one | 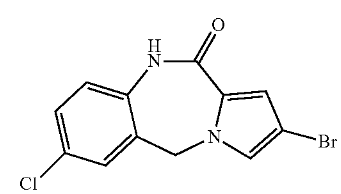 | 312.93 |
| 35 | 7-Methyl-2-(trifluoromethyl)-5,10-dihydro-11H-pyrrolo[2,1-c][1,4]benzodiazepin-11-one | 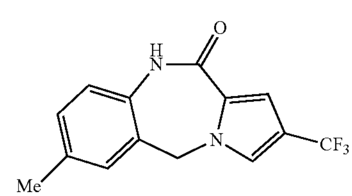 | 281.14 |

-continued

| Preparation No. | Name | Structure | MS (m/z): (M + 1). |
|---|---|---|---|
| 36 | 2,7-Dichloro-5,10-dihydro-11H-pyrrolo[2,1-c][1,4]benzodiazepin-11-one | 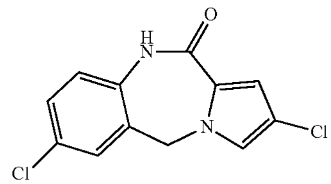 | 267.04 |
| 37 | 7-Chloro-2-(methylsulfanyl)-5,10-dihydro-11H-pyrrolo[2,1-c][1,4]benzodiazepin-11-one | 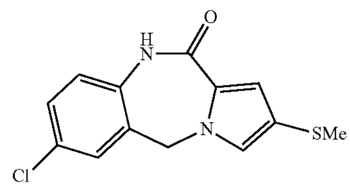 | 279.04 [M + H]+ 579.02 [2M + Na]+ |
| 38 | 2-Bromo-7-methyl-5,10-dihydro-11H-pyrrolo[2,1-c][1,4]benzodiazepin-11-one | 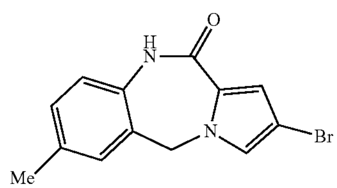 | 291.04/ 292.99 |
| 39 | 7-Chloro-2-(1-methylethyl)-5,10-dihydro-11H-pyrrolo[2,1-c][1,4]benzodiazepin-11-one | 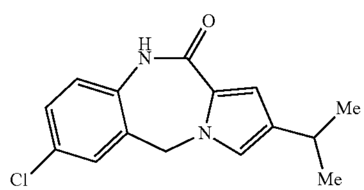 | 275.19 |
| 40 | 7-Chloro-2-(trifluoromethyl)-5,10-dihydro-11H-pyrrolo[2,1-c][1,4]benzodiazepin-11-one | 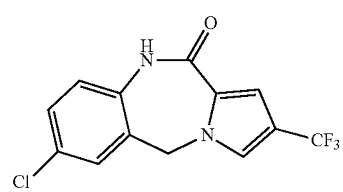 | 300.99 |
| 41 | 7-Chloro-2-ethyl-5,10-dihydro-11H-pyrrolo[2,1-c][1,4]benzodiazepin-11-one | 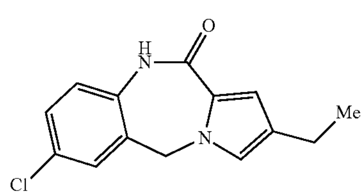 | 261.19 |
| 42 | 1-Methoxy-2,7-dimethyl-5,10-dihydro-11H-pyrrolo[2,1-c][1,4]benzodiazepin-11-one | 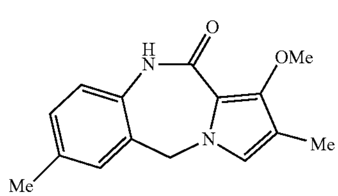 | 257.14 |

PREPARATION 43

Alternative synthesis of 7-chloro-2-(trifluoromethyl)-5,10-dihydro-11H-pyrrolo[2,1-c][1,4]benzodiazepin-11-one

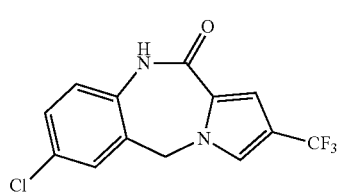

Add tin dichloride (3 equiv; 3.02 g, 15.77 mmol) in 5M hydrochloric acid (20 mL, 100 mmol) to ethyl 1-(5-chloro-2-nitrobenzyl)-4-(trifluoromethyl)-1H-pyrrole-2-carboxylate (1 equiv; 1.98 g, 5.26 mmoles) and ethanol (100 mL) at 50° C. Heat overnight and then for a further 26 h, remove most of the ethanol in vacuo and dilute the resultant solution with water and collect the resultant precipitate by filtration, wash well with water and dry in vacuo at 40° C. Absorb the solid onto silica, chromatograph eluting with DCM/methanol (5:95) to give uncyclised amino ester (0.260 g) and 7-chloro-2-(trifluoromethyl)-5,10-dihydro-11H-pyrrolo[2,1-c][1,4]benzodiazepin-11-one (0.613 g). Heat the uncyclised ester in a mixture of 5M hydrochloric acid (10 mL, 50 mmol) for 80 h. Remove the ethanol in vacuo and collect the resultant precipitated solid by filtration and wash with water to give 7-chloro-2-(trifluoromethyl)-5,10-dihydro-11H-pyrrolo[2,1-c][1,4]benzodiazepin-11-one (0.17 g). Combine with earlier 7-chloro-2-(trifluoromethyl)-5,10-dihydro-11H-pyrrolo[2,1-c][1,4]benzodiazepin-11-one to give (0.794 g, 50% yield). MS (m/z): 300.99 (M+1).

The following compound is prepared essentially by the method of Preparation 43.

PREPARATION 45

Synthesis of 7,11-dichloro-2-methyl-5H-pyrrolo[2,1-c][1,4]benzodiazepine

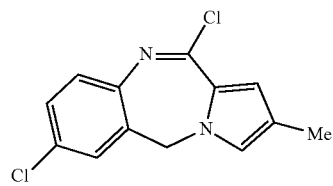

To a suspension of 7-chloro-2-methyl-5,10-dihydro-11H-pyrrolo[2,1-c][1,4]benzodiazepin-11-one (40.6 g, 164.58 mmoles) in methoxybenzene (250 mL) at 70° C. add N,N-dimethylaniline (2.8 equiv; 58.59 mL, 460.8 mmoles) in one portion followed by phosphoryl chloride (2.3 equiv (molar); 35.18 mL, 378.52 mmoles) over 20 minutes, controlling the exotherm by addition. Heat the resultant dark solution at 90° C. for 1.5 h. Add additional phosphoryl chloride (0.33 equiv; 5.05 mL, 54.31 mmoles) and heat the mixture at 90° C. for a further 1 h to give complete conversion. Evaporate to near dryness and partition the residue between water (500 mL) and ethyl acetate (2×500 mL). Combine organic layers and wash with water (500 mL) then brine. Dry over $Na_2SO_4$, filter and evaporate onto silica. Pass through a silica gel pad with iso-hexane/ethyl acetate (gradient elution 5 to 25%). Combine product fractions and evaporate to a small amount of solvent. Add iso-hexane (150 mL) and collect the resulting yellow powder by filtration, to give 7,11-dichloro-2-methyl-5H-pyrrolo[2,1-c][1,4]benzodiazepine (34.0 g, 78% yield). MS (m/z): 265.1 (M+1).

Alternative synthesis:

Under a $N_2$ atmosphere add phosphoryl chloride (124 g, 819 mmol) to a mixture of 7-chloro-2-methyl-5,10-dihydro-11H-pyrrolo[2,1-c][1,4]benzodiazepin-11-one (100 g, 405 mmol), N,N-dimethylaniline (138 g, 1.14 mol) and anisole (550 mL). Heat to 80-85° C. and stir for 4 hr. to 6 hr. Concentrate to a total of 1.5 volumes to 2.5 volumes while maintaining the temperature below 75° C. Cool to 15-25° C. Add dichloromethane (600 mL) dropwise and stir for 1 hr. Add the

| Preparation No. | Name | Intermediate | MS (m/z): (M + 1). |
|---|---|---|---|
| 44 | 7-Chloro-1-methoxy-2-methyl-5,10-dihydro-11H-pyrrolo[2,1-c][1,4]benzodiazepin-11-one | 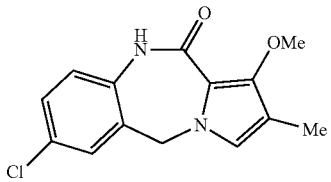 | 277.09 | resulting mixture to water (600 mL) while maintaining the temperature between 10° C. and 35° C. Stir for 1 hr. and then separate the layers. Extract the aqueous layer with dichloromethane (600 mL). Wash the combined organic layers with 1.0 N HCl (600 g) followed by 7% NaHCO$_3$ (600 g). Filter the organic layer through diatomite (20 g to 30 g) and silica gel (60 g to 100 g). Concentrate the resulting filtrate to a total of 1.5 volumes to 2.5 volumes while maintaining the temperature below 45° C. Add heptane (270 g to 410 g) and concentrate the resulting filtrate to a total of 1.5 volumes to 2.5 volumes while maintaining the temperature below 45° C. Add heptane (150 g to 210 g), cool to 5° C. to 10° C., and stir for 2 hr. to 3 hr. Filter, rinse the filter the cake with heptane, and dry under vacuum, at below 45° C., to obtain the title compound as a pale yellow solid (90% to 95% yield)

The following compounds are prepared essentially by the method of Preparation 45.

| Preparation No. | Name | Structure | MS (m/z): (M + 1). |
|---|---|---|---|
| 46 | 2,11-Dichloro-7-methyl-5H-pyrrolo[2,1-c][1,4]benzodiazepine | 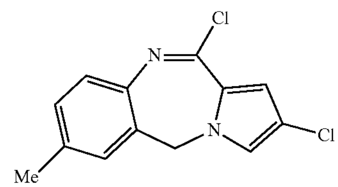 | 265.09/267.04 |
| 47 | 7,11-Dichloro-1-methoxy-2-methyl-5H-pyrrolo[2,1-c][1,4]benzodiazepine | 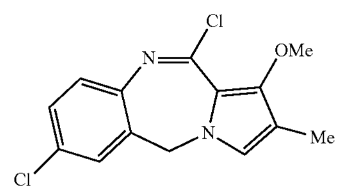 | 295.09/297.04 |
| 48 | 11-Chloro-2,7-dimethyl-1-methoxy-5H-pyrrolo[2,1-c][1,4]benzodiazepine | 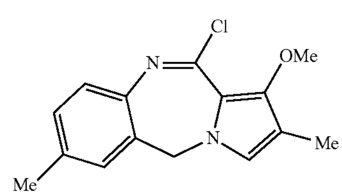 | 275.14/277.09 |
| 49 | 2-Bromo-11-chloro-7-methyl-5H-pyrrolo[2,1-c][1,4]benzodiazepine | 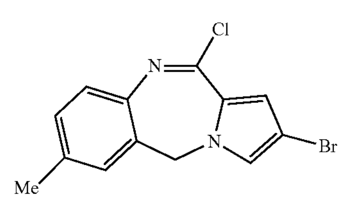 | 309.04/310.98 |

PREPARATION 50

Synthesis of methyl 3-[4-(7-chloro-2-methyl-5H-pyrrolo[2,1-c][1,4]benzodiazepin-11-yl)piperazin-1-yl]-2,2-dimethylpropanoate

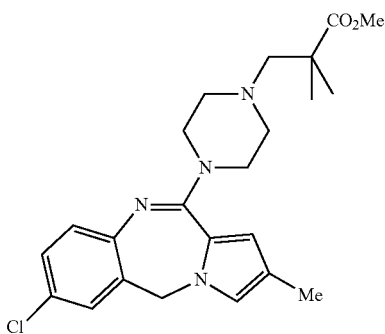

Add phosphoryl chloride (1.47 mL, 2.43 g, 15.85 mmoles) to 7-chloro-2-methyl-5,10-dihydro-11H-pyrrolo[2,1-c][1,4]benzodiazepin-11-one (1.117 g, 4.53 mmoles) in DCM (50 mL) and stir at room temperature over a weekend. Add ice water to the reaction mixture then add DCM, separate the aqueous layer and wash the DCM layer with water and sodium hydrogen carbonate solution. Dry the DCM solution with $MgSO_4$, filter and evaporate the solvent in vacuo to give 7,11-dichloro-2-methyl-5H-pyrrolo[2,1-c][1,4]benzodiazepine (1.167 g).

Dissolve methyl 2,2-dimethyl-3-(piperazin-1-yl)propanoate dihydrochloride (1.61 g, 5.89 mmoles) in water and load on to two SCX-2 (10 g) cartridges. Wash the cartridges with methanol and elute with 2M ammonia in methanol. Concentrate in vacuo, then dissolve the resultant oil in acetonitrile (40 mL). Add 7,11-dichloro-2-methyl-5H-pyrrolo[2,1-c][1,4]benzodiazepine (1.167 g, 4.4 mmoles) to the acetonitrile solution. Divide the acetonitrile solution and place in to 2 microwave tubes, add potassium carbonate (0.89 g, 6.79 mmoles) to each microwave tube and heat and stir at 140° C. in the microwave for 3.5 hr. Allow the reaction mixture to cool, filter, wash the solid collected on the sinter with acetonitrile then concentrate the filtrate in vacuo, add methanol and then evaporate to dryness. Treat with more methanol and collect the resultant precipitate, wash the precipitate with methanol to give methyl 3-[4-(7-chloro-2-methyl-5H-pyrrolo[2,1-c][1,4]benzodiazepin-11-yl)piperazin-1-yl]-2,2-dimethylpropanoate as a crystalline solid (1.1 g). MS (m/z): 429.18 (M+1).

Alternative synthesis of methyl 3-[4-(7-chloro-2-methyl-5H-pyrrolo[2,1-c][1,4]benzodiazepin-11-yl)piperazin-1-yl]-2,2-dimethylpropanoate.

To a suspension of 7,11-dichloro-2-methyl-5H-pyrrolo[2,1-c][1,4]benzodiazepine (34.0 g, 128.23 mmoles) in acetonitrile (300 mL) add methyl 2,2-dimethyl-3-(piperazin-1-yl)-propanoate hydrochloride (2.1 equiv; 63.75 g, 269.29 mmoles) and potassium carbonate (4 equiv; 70.89 g, 512.93 mmoles). Heat the mixture at reflux overnight. Evaporate to dryness. Partition the residue between water (500 mL) and EtOAc (2×500 mL). Combine the organic layers and wash with water (500 mL) then brine. Dry over sodium sulfate, filter and evaporate to a brown oil. Add iso-hexane (~150 mL) and a seed crystal of Preparation 50. Allow to crystallize over 2 h, then transfer the flask to a fridge and allow to stand. Collect the resulting heavy crystalline solid by filtration, washing with cold iso-hexane. Dry in a vacuum oven at 40° C. for 1 h, to give methyl 3-[4-(7-chloro-2-methyl-5H-pyrrolo[2,1-c][1,4]benzodiazepin-11-yl)piperazin-1-yl]-2,2-dimethylpropanoate (53.6 g, 97% yield). MS (m/z): 429.18 (M+1).

Second alternative synthesis of methyl 3-[4-(7-chloro-2-methyl-5H-pyrrolo[2,1-c][1,4]benzodiazepin-11-yl)piperazin-1-yl]-2,2-dimethylpropanoate.

Heat a mixture of 7,11-dichloro-2-methyl-5H-pyrrolo[2,1-c][1,4]benzodiazepine (10.0 g, 37.7 mmol), methyl 2,2-dimethyl-3-(piperazin-1-yl)-propionate dihydrochloride (19.4 g, 71.0 mmol), diisopropylamine (22.9 g, 226 mmol), and acetonitrile (80 g) at 80° C. to 85° C. for 22 hr. to 26 hr. Cool to 30° C. to 40° C. and add ethyl acetate (80 g). Add water (80 g) dropwise. Stir 40 min. to 60 min. and separate the layers. Extract the aqueous layer with ethyl acetate (60 g to 80 g). Wash the combined organic layers with 25% aqueous sodium chloride (2×40 g). Concentrate the organic layer to a total of 1.5 volumes and 3.5 volumes while maintaining the temperature below 50° C. Add heptane (41 g to 55 g) at 40° C. to 50° C.)\ and stir for 2 hr. to 3 hr. Concentrate to a total of 1.5 volumes to 3.0 volumes while maintaining the temperature below 50° C. Cool to 0° C. to 10° C. and stir for 2 hr. to 3 hr. Filter, wash the filtercake with heptane (3.0 g to 10.0 g), and dry under vacuum, at below 60° C., to afford the title compound (16.0 g, 94.7% w/w % assay, 94% yield) as a light, yellow solid.

PREPARATION 51

Synthesis of methyl 3-[4-(2,7-dichloro-5H-pyrrolo[2,1-c][1,4]benzodiazepin-11-yl)piperazin-1-yl]-2,2-dimethylpropanoate

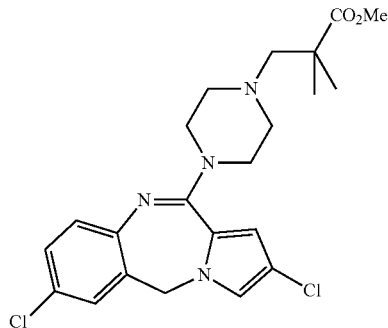

Add phosphoryl chloride (5 equiv; 4.36 mL, 7.19 g, 46.89 mmoles) to 2,7-dichloro-5,10-dihydro-11H-pyrrolo[2,1-c][1,4]benzodiazepin-11-one (1 equiv; 2.505 g, 9.38 mmoles) in chloroform (80 mL) and heat and stir at 50° C. overnight. Decant the reaction solution and evaporate in vacuo to an oil. Dissolve the oil in DCM, wash with saturated aqueous sodium hydrogen carbonate solution. Dry the DCM solution over $Na_2SO_4$, filter and concentrate to dryness to give 2,7,11-trichloro-5H-pyrrolo[2,1-c][1,4]benzodiazepine as a cream colored solid. In parallel desalt methyl 2,2-dimethyl-3-(piperazin-1-yl)propanoate hydrochloride (0.837 g, 3.54 mmoles) by dissolving in methanol, add the methanolic solution to an SCX-2 column (10 g) wash with methanol and then elute with 2.5M ammonia in methanol solution, evaporate the methanol ammonia fraction to give methyl 2,2-dimethyl-3-(piperazin-1-yl)propanoate (0.665 g) as an oil. Mix this oil with 2,7,11-trichloro-5H-pyrrolo[2,1-c][1,4]benzodiazepine (0.505 g 1.77 mmoles), potassium carbonate (0.733 g, 5.31 mmoles) and acetonitrile (20 mL) and heat at reflux overnight. Cool the reaction mixture to room temperature and filter, washing the sinter with EtOAc, then evaporate the filtrate in vacuo to a solid. Chromatograph on silica eluting with methanol/DCM (gradient elution 2:98 to 8:92). Evaporate the fractions containing product to give methyl 3-[4-(2,7-dichloro-5H-pyrrolo[2,1-c][1,4]benzodiazepin-11-yl)piperazin-1-yl]-2,2-dimethylpropanoate (0.69 g). MS (m/z): 449.13/451.07 (M+1).

The following compounds are prepared essentially by the method of Preparation 51.

| Preparation No. | Name | Structure | MS (m/z): (M + 1). |
|---|---|---|---|
| 52 | Methyl 3-[4-(2,7-dimethyl-5H-pyrrolo[2,1-c][1,4]benzodiazepin-11-yl)piperazin-1-yl]-2,2-dimethylpropanoate | 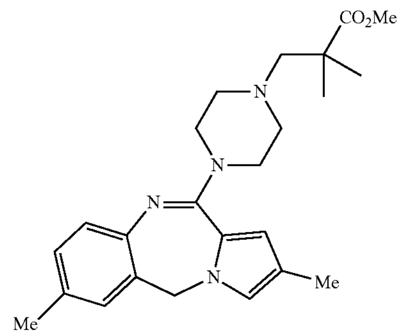 | 409.23 |
| 53 | Methyl 3-[4-(2-bromo-7-chloro-5H-pyrrolo[2,1-c][1,4]benzodiazepin-11-yl)piperazin-1-yl]-2,2-dimethylpropanoate | 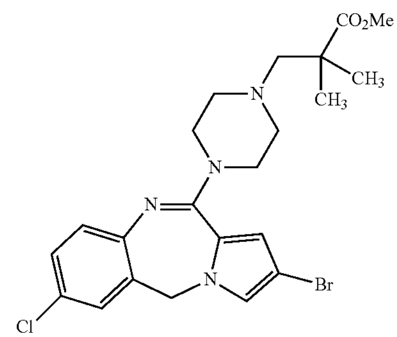 | 493.00/ 495.00 |
| 54 | Methyl 3-[4-(7-chloro-2-ethyl-5H-pyrrolo[2,1-c][1,4]benzodiazepin-11-yl)piperazin-1-yl]-2,2-dimethylpropanoate | 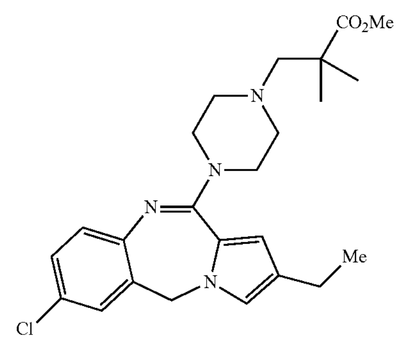 | 443.18 |
| 55 | Methyl 2,2-dimethyl-3-[4-(7-methyl-2-(trifluoromethyl)-5H-pyrrolo[2,1-c][1,4]benzodiazepin-11-yl)piperazin-1-yl]-propanoate | 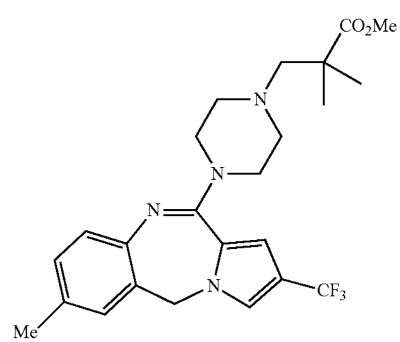 | 463.17 |

-continued

| Preparation No. | Name | Structure | MS (m/z): (M + 1). |
|---|---|---|---|
| 56 | Methyl 3-[4-(7-chloro-2-(trifluoromethyl)-5H-pyrrolo[2,1-c][1,4]benzodiazepin-11-yl)piperazin-1-yl]-2,2-dimethylpropanoate | 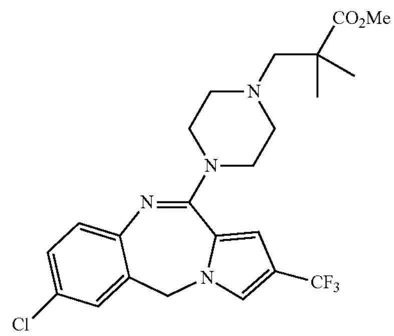 | 483.17 |
| 57 | Methyl 3-[4-(7-chloro-2-(1-methylethyl)-5H-pyrrolo[2,1-c][1,4]benzodiazepin-11-yl)piperazin-1-yl]-2,2-dimethylpropanoate | 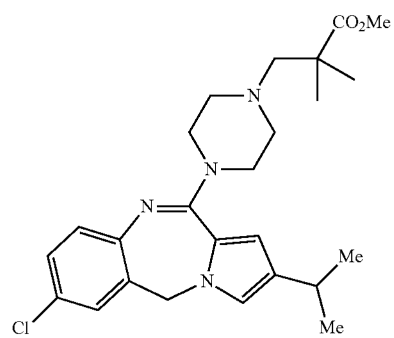 | 457.07/ 459.17 |
| 58 | Methyl 2,2-dimethyl-3-[4-(7-methyl-2-(trifluoromethyl)-5H-pyrrolo[2,1-c][1,4]benzodiazepin-11-yl)piperazin-1-yl]-propanoate | 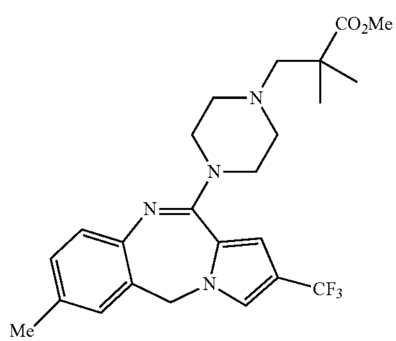 | 463.17 |
| 59 | Methyl 3-[4-(2-bromo-7-methyl-5H-pyrrolo[2,1-c][1,4]benzodiazepin-11-yl)piperazin-1-yl]-2,2-dimethylpropanoate | 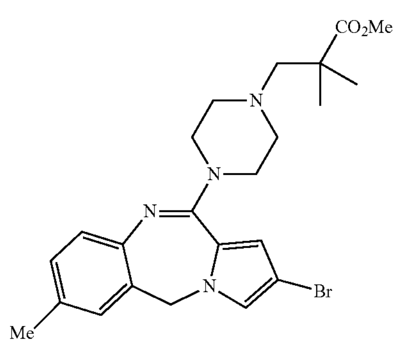 | 473.12/ 475.07 |

PREPARATION 60

Synthesis of methyl 2,2-dimethyl-3-[4-(7-methyl-2-(methylsulfanyl)-5H-pyrrolo[2,1-c][1,4]benzodiazepin-11-yl)piperazin-1-yl]-propanoate

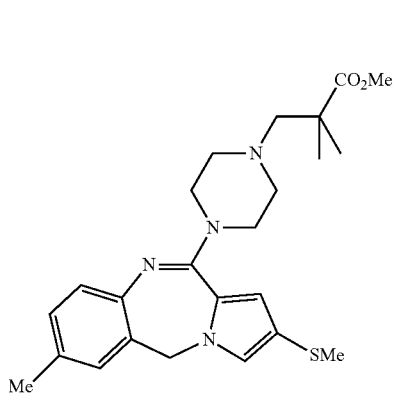

Treat methyl 1-(5-methyl-2-nitrobenzyl)-4-(methylsulfanyl)-1H-pyrrole-2-carboxylate (3.49 mmoles; 1.12 g) with acetic acid (15 mL) then treat with iron, powder (10.5 mmoles; 585 mg) then slowly heat in an oil bath at 80° C. After a few hours increase the oil bath temperature to 90° C. Then leave the reaction at 60° C. for 2 days. Then concentrate to dryness to remove acetic acid then treat with EtOAc and wash through a pad of silica with more EtOAc until the orange colour stops coming off. Concentrate the red eluant to dryness then treat with methanol then re-concentrate and dissolve in DCM (20 mL) and treat with phosphoryl chloride (1.0 mL). Heat the reaction in an oil bath at 50° C. overnight. Then cool the reaction to RT and treat with ice then wash with water twice and then NaHCO₃ (aq). Dry the organic layer over MgSO₄, filter and concentrate to a tar. Meanwhile dissolve methyl 2,2-dimethyl-3-(piperazin-1-yl)-propanoate dihydrochloride (1.60 g, 5.86 mmoles) in water then load on to a SCX-2 cartridge (2×10 g) and wash with methanol and then elute with ammonia in methanol. Concentrate the basic solution to dryness to an oil. Then dissolve this oil in acetonitrile (50 mL) and add to a mixture of the tar and potassium carbonate (1.0 g) then heat to reflux. After 2 hours, microwave the reaction to 140° C. for 2 hours. Then filter the reaction and extract with acetonitrile and acetone. Combine and concentrate the mother liquors to dryness onto silica then purify by flash chromatography silica (40 g) (10-50% EtOAc in hexane). Take the fractions which contain clean product, combine and concentrate to yield methyl 2,2-dimethyl-3-[4-(7-methyl-2-(methylsulfanyl)-5H-pyrrolo[2,1-c][1,4]benzodiazepin-11-yl)piperazin-1-yl]-propanoate (418 mg; 27% yield). MS (m/z): 441.18 (M+1).

PREPARATION 61

Synthesis of 7-chloro-2-(methylsulfanyl)-11-(piperazin-1-yl)-5H-pyrrolo[2,1-c][1,4]benzodiazepine

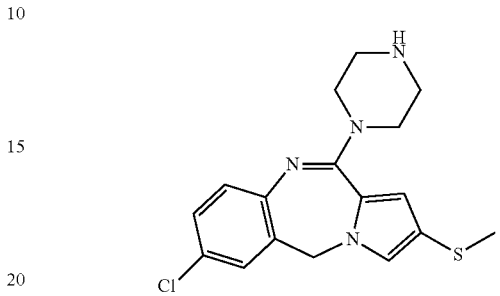

Add phosphoryl chloride (5 equiv; 2.21 mL, 3.64 g, 23.76 mmoles) to 7-chloro-2-(methylsulfanyl)-5,10-dihydro-11H-pyrrolo[2,1-c][1,4]benzodiazepin-11-one (1.38 g, 4.75 mmoles) in chloroform (20 mL) and heat and stir at 45° C. for 2 h. Raise the temperature of the reaction to 60° C. and stir for a further 2 h. Remove the chloroform in vacuo and dissolve the residue in DCM (100 mL) and wash with saturated sodium bicarbonate solution (100 mL). Filter the DCM layer through a phase separation frit and evaporate the solvent in vacuo to give a viscous oil. Dissolve the oil in acetonitrile (10 mL) and add cesium carbonate (3 equiv; 4.65 g, 14.26 mmoles). Add to this mixture piperazine (10 equiv; 4.09 g, 47.52 mmoles) in dry acetonitrile (10 mL) and heat and stir the mixture under reflux overnight. Cool the reaction mixture and add saturated ammonium chloride solution (100 mL) and extract into EtOAc (2×50 mL). Combine the organic layers and wash with water (3×100 mL), dry over MgSO₄, filter and evaporate the solvent in vacuo to give 7-chloro-2-(methylsulfanyl)-11-(piperazin-1-yl)-5H-pyrrolo[2,1-c][1,4]benzodiazepine (1.0 g, 60%). MS (m/z): 347.13 (M+1).

PREPARATION 62

Synthesis of methyl 3-[4-(7-chloro-2-(methylsulfanyl)-5H-pyrrolo[2,1-c][1,4]benzodiazepin-11-yl)piperazin-1-yl]-2,2-dimethylpropanoate

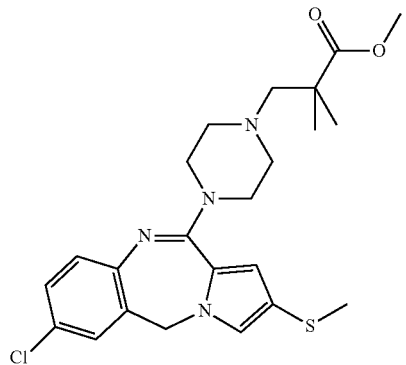

Add methyl 2,2-dimethyl-3-oxo-propanoate (0.928 g, 7.13 mmoles) in DCM (5 mL) to 7-chloro-2-(methylsulfanyl)-11-(piperazin-1-yl)-5H-pyrrolo[2,1-c][1,4]benzodiazepine (1.0 g, 2.85 mmoles) in DCM (10 mL) and stir under nitrogen for 30 minutes at room temperature. Add sodium triacetoxyborohydride (3 equiv; 1.89 g, 8.56 mmoles) to the reaction mixture and stir under nitrogen overnight at room temperature. Add methanol and apply to an SCX-2 column, wash with methanol and elute with 2M ammonia in methanol. Evaporate the methanol solution to give methyl 3-[4-(7-chloro-2-(methylsulfanyl)-5H-pyrrolo[2,1-c][1,4]benzodiazepin-11-yl)piperazin-1-yl]-2,2-dimethylpropanoate (1.23 g, 84%). MS (m/z): 461.12 (M+1).

PREPARATION 63

Synthesis of methyl 2,2-dimethyl-3-{4-[7-methyl-2-(propan-2-yl)-5H-pyrrolo[2,1-c][1,4]benzodiazepin-11-yl]piperazin-1-yl]propanoate Mix methyl 3-[4-(2-bromo-7-methyl-5H-pyrrolo[2,1-c][1,4]benzodiazepin-11-yl)piperazin-1-yl]-2,2-dimethylpropanoate (1.00 equiv; 600.00 mg, 1.27 mmoles), 4,4,5,5-tetramethyl-2-(prop-1-en-2-yl)-1,3,2-dioxaborolane (3.00 equiv; 638.93 mg, 3.80 mmoles) in methanol (15 mL). Add a pre-blended mixture of 1.09 wt % tris(dibenzylideneacetonyl)bis-palladium (Pd$_2$(dba)$_3$), 1.16 wt % 1,1'-bis(di-tert-butylphosphino)ferrocene (dtbpf) and 97.75 wt % tripotassium phosphate (1.06 g) and heat at 140° C. for 25 mins in a microwave. Filter the reaction mixture through celite and dilute to 25 mL volume with methanol. Hydrogenate the methanolic solution by passing at 1 mL/min. through a H-Cube® flow hydrogenator using a 10% Pd/C catalytic cartridge at 50° C. Evaporate the solvent in vacuo to give methyl 2,2-dimethyl-3-{4-[7-methyl-2-(propan-2-yl)-5H-pyrrolo[2,1-c][1,4]benzodiazepin-11-yl]piperazin-1-yl}propanoate. MS (m/z): 437.28 (M+1).

PREPARATION 64

Synthesis of methyl 3-[4-(2-ethyl-7-methyl-5H-pyrrolo[2,1-c][1,4]benzodiazepin-11-yl)piperazin-1-yl]-2,2-dimethylpropanoate

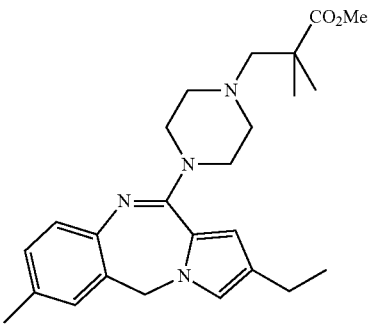

Mix methyl 3-[4-(2-bromo-7-methyl-5H-pyrrolo[2,1-c][1,4]benzodiazepin-11-yl)piperazin-1-yl]-2,2-dimethylpropanoate (1.00 equiv; 620.00 mg, 1.31 mmoles), triethenylboroxin pyridine (1.5 equiv; 472.79 mg, 1.96 mmoles;) in methanol (15 mL). Add a pre-blended mixture of 1.09 wt % tris(dibenzylideneacetonyl)bis-palladium (Pd$_2$(dba)$_3$), 1.16 wt % 1,1'-bis(di-tert-butylphosphino)ferrocene (dtbpf) and 97.75 wt % tripotassium phosphate (1.10 g) and heat at 140° C. for 25 mins in a microwave. Filter the reaction mixture through celite and dilute to 25 mL volume with methanol. Hydrogenate the methanolic solution by passing at 1 mL/min. through a H-Cube® flow hydrogenator using a 10% Pd/C catalytic cartridge at 50° C. Evaporate the solvent in vacuo to give methyl 3-[4-(2-ethyl-7-methyl-5H-pyrrolo[2,1-c][1,4]benzodiazepin-11-yl)piperazin-1-yl]-2,2-dimethylpropanoate. MS (m/z): 423.18 (M+1).

EXAMPLE 1

Synthesis of 3-[4-(7-chloro-2-methyl-5H-pyrrolo[2,1-c][1,4]benzodiazepin-11-yl)piperazin-1-yl]-2,2-dimethylpropanoic acid

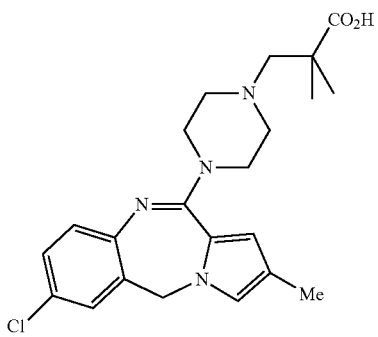

To a suspension of methyl 3-[4-(7-chloro-2-methyl-5H-pyrrolo[2,1-c][1,4]benzodiazepin-11-yl)piperazin-1-yl]-2,2-dimethylpropanoate (28.0 g, 65.27 mmoles) in a mixture of isopropyl alcohol (150 mL) and water (150 mL) add sodium hydroxide (3 equiv; 7.83 g, 195.82 mmoles) and heat at 70° C. for 4 h to give a clear solution. Heat at 70° C. for a further 1 h then cool slightly. Add 5M hydrochloric acid to give pH 8 and precipitate a white solid. Add further 5M hydrochloric acid to give a pH between 6.5 and 7. Reduce the volume of solvent by half and then chill the flask in a fridge for 0.5 h. Collect the resulting white solid by filtration and dry overnight in a vacuum oven at 40° C. over phosphorus pentoxide to give 3-[4-(7-chloro-2-methyl-5H-pyrrolo[2,1-c][1,4]benzodiazepin-11-yl)piperazin-1-yl]-2,2-dimethylpropanoic acid (26.5 g, 98% yield). MS (m/z): 415.3 (M+1). DSC melting point=246.5° C. (onset).

The following compounds are prepared essentially by the method of Example 1.

| Example No. | Name | Structure | MS (m/z): (M + 1). |
|---|---|---|---|
| 2 | 3-[4-(2,7-Dimethyl-5H-pyrrolo[2,1-c][1,4]benzodiazepin-11-yl)piperazin-1-yl]-2,2-dimethylpropanoic acid | 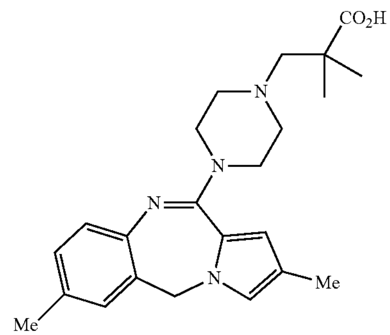 | 395.28 |
| 3 | 3-[4-(2-Bromo-7-chloro-5H-pyrrolo[2,1-c][1,4]benzodiazepin-11-yl)piperazin-1-yl]-2,2-dimethylpropanoic acid | 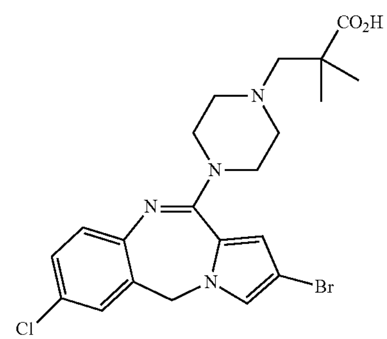 | 480.97 |
| 4 | 3-[4-(7-Chloro-2-ethyl-5H-pyrrolo[2,1-c][1,4]benzodiazepin-11-yl)piperazin-1-yl]-2,2-dimethylpropanoic acid | 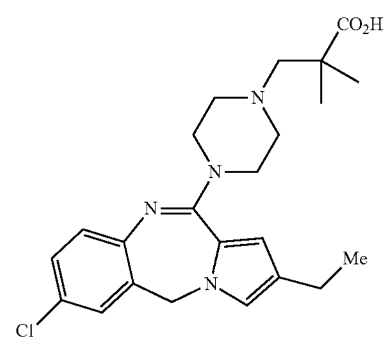 | 429.18 |
| 5 | 2,2-Dimethyl-3-{4-[7-methyl-2-(trifluoromethyl)-5H-pyrrolo[2,1-c][1,4]benzodiazepin-11-yl]piperazin-1-yl}propanoic acid | 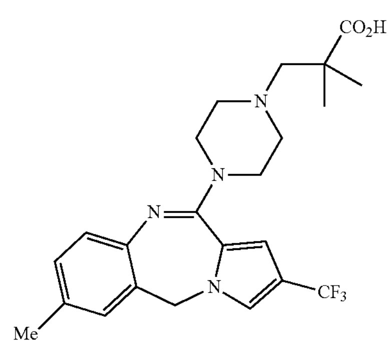 | 449.18 |

-continued

| Example No. | Name | Structure | MS (m/z): (M + 1). |
|---|---|---|---|
| 6 | 3-[4-(7-Chloro-2-(trifluoromethyl)-5H-pyrrolo[2,1-c][1,4]benzodiazepin-11-yl)piperazin-1-yl]-2,2-dimethylpropanoic acid | 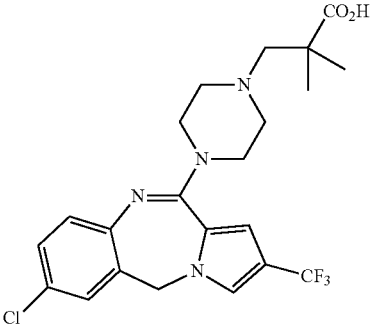 | 468.62 |
| 7 | 3-[4-(2,7-Dichloro-5H-pyrrolo[2,1-c][1,4]benzodiazepin-11-yl)piperazin-1-yl]-2,2-dimethylpropanoic acid | 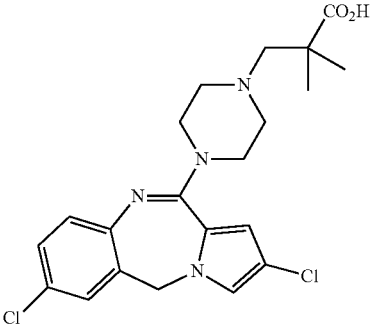 | 435.18 |
| 8 | 3-[4-(7-Chloro-2-(methylsulfanyl)-5H-pyrrolo[2,1-c][1,4]benzodiazepin-11-yl)piperazin-1-yl]-2,2-dimethylpropanoic acid | 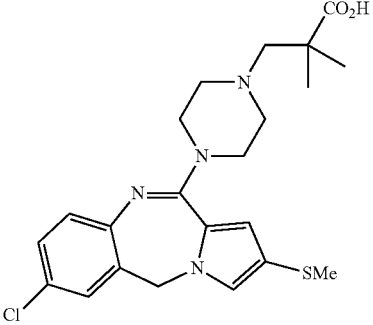 | 447.17 |
| 9 | 2,2-Dimethyl-3-{4-[7-methyl-2-(propan-2-yl)-5H-pyrrolo[2,1-c][1,4]benzodiazepin-11-yl]piperazin-1-yl}propanoic acid | 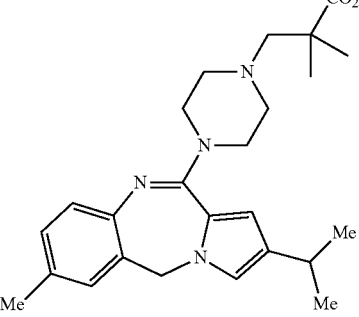 | 423.17 |

-continued

| Example No. | Name | Structure | MS (m/z): (M + 1). |
|---|---|---|---|
| 10 | 3-[4-(2-Ethyl-7-methyl-5H-pyrrolo[2,1-c][1,4]benzodiazepin-11-yl)piperazin-1-yl]-2,2-dimethylpropanoic acid | 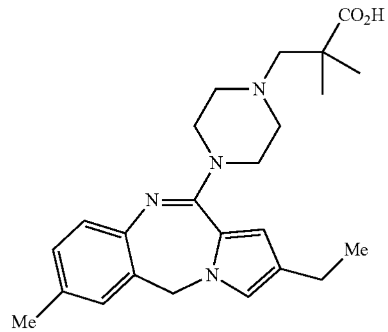 | 409.18 |
| 11 | 3-{4-[7-Chloro-2-(propan-2-yl)-5H-pyrrolo[2,1-c][1,4]benzodiazepin-11-yl]piperazin-1-yl}-2,2-dimethylpropanoic acid | 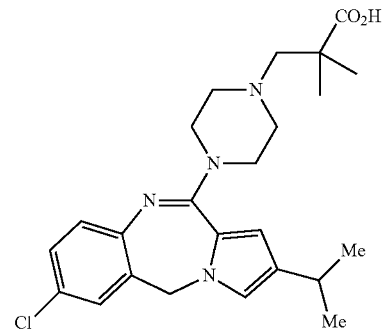 | 443.18 |
| 12 | 2,2-Dimethyl-3-{4-[7-methyl-2-(methylsulfanyl)-5H-pyrrolo[2,1-c][1,4]benzodiazepin-11-yl]piperazin-1-yl}propanoic acid | 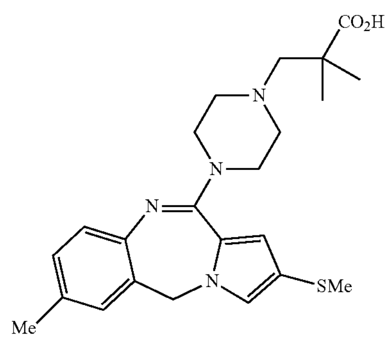 | 427.18 |

EXAMPLE 13

Synthesis of 3-[4-(7-Chloro-2-methyl-5H-pyrrolo[2,1-c][1,4]benzodiazepin-11-yl)piperazin-1-yl]-2,2-dimethylpropanoic acid dihydrochloride

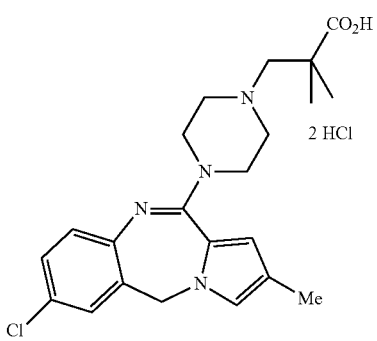

To a suspension of 3-[4-(7-chloro-2-methyl-5H-pyrrolo[2,1-c][1,4]benzodiazepin-11-yl)piperazin-1-yl]-2,2-dimethylpropanoic acid (24.25 g, 58.44 mmoles) in isopropyl alcohol (250 mL) at 60° C., add a 4M dioxane solution of hydrogen chloride (2.4 equiv; 35.07 mL, 140.26 mmoles) over 10 minutes to give a clear solution. Allow to cool slightly then evaporate to an off-white solid. Triturate with a small amount of diethyl ether and collect the powdery cream solid by filtration. Dry in a vacuum oven at 40° C. overnight. Grind to a fine powder and dry in a vacuum oven at 60° C. for 6 h. Monitor levels of residual isopropyl alcohol by $^1$H NMR. Dissolve in warm ethanol (350 mL) and evaporate to dryness. Triturate with ethanol (50 mL) and evaporate to dryness again. Triturate with dry diethyl ether (200 mL) and collect the resulting solid by filtration. Dry for 6 h in a vacuum oven at 50° C. to give 3-[4-(7-chloro-2-methyl-5H-pyrrolo[2,1-c][1,4]benzodiazepin-11-yl)piperazin-1-yl]-2,2-dimethylpropanoic acid dihydrochloride (26.9 g, 94% yield) MS (m/z): 415.2 (M+1).

The following compounds are prepared essentially by the method of Example 13.

| Example No. | Name | Structure | MS (m/z): (M + 1). |
|---|---|---|---|
| 14 | 3-[4-(2,7-Dimethyl-5H-pyrrolo[2,1-c][1,4]benzodiazepin-11-yl)piperazin-1-yl]-2,2-dimethylpropanoic acid dihydrochloride | 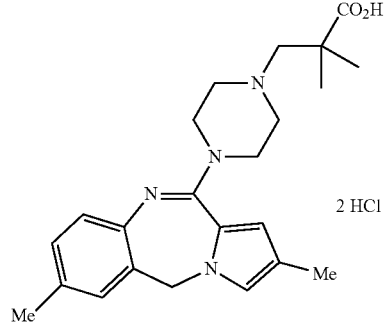 | 395.28 |
| 15 | 3-[4-(2-Bromo-7-chloro-5H-pyrrolo[2,1-c][1,4]benzodiazepin-11-yl)piperazin-1-yl]-2,2-dimethylpropanoic acid dihydrochloride | 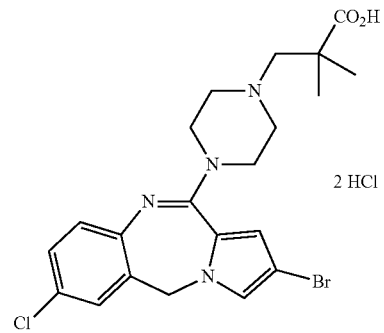 | 480.97 |
| 16 | 3-[4-(7-Chloro-2-ethyl-5H-pyrrolo[2,1-c][1,4]benzodiazepin-11-yl)piperazin-1-yl]-2,2-dimethylpropanoic acid dihydrochloride | 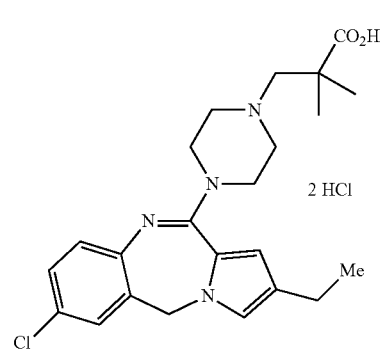 | 429.18 |
| 17 | 2,2-Dimethyl-3-{4-[7-methyl-2-(trifluoromethyl)-5H-pyrrolo[2,1-c][1,4]benzodiazepin-11-yl]piperazin-1-yl}propanoic acid dihydrochloride | 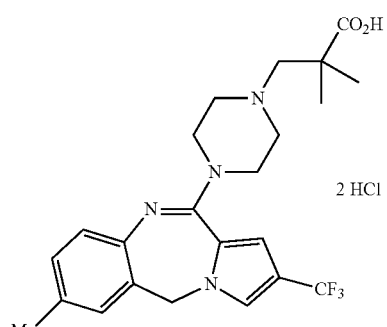 | 449.18 |

-continued

| Example No. | Name | Structure | MS (m/z): (M + 1). |
|---|---|---|---|
| 18 | 3-{4-[7-Chloro-2-(trifluoromethyl)-5H-pyrrolo[2,1-c][1,4]benzodiazepin-11-yl]piperazin-1-yl}-2,2-dimethylpropanoic acid dihydrochloride | 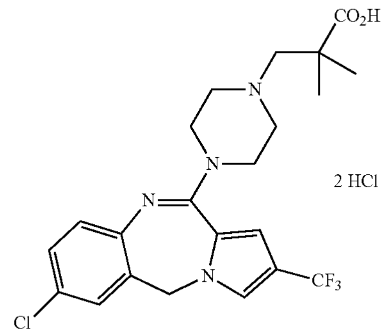 | 469.07 |
| 19 | 3-[4-(2,7-Dichloro-5H-pyrrolo[2,1-c][1,4]benzodiazepin-11-yl)piperazin-1-yl]-2,2-dimethylpropanoic acid dihydrochloride | 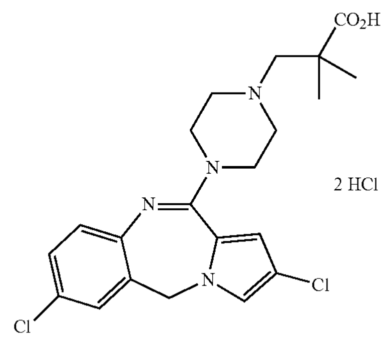 | 434.68 |
| 20 | 3-{4-[7-Chloro-2-(methylsulfanyl)-5H-pyrrolo[2,1-c][1,4]benzodiazepin-11-yl]piperazin-1-yl}-2,2-dimethylpropanoic acid hydrochloride | 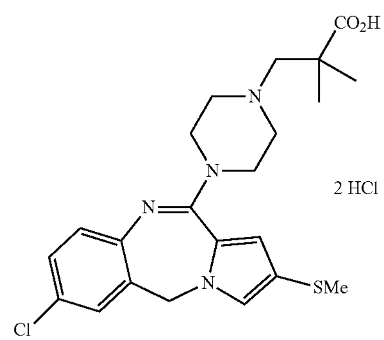 | 446.98 |
| 21 | 2,2-Dimethyl-3-{4-[7-methyl-2-(propan-2-yl)-5H-pyrrolo[2,1-c][1,4]benzodiazepin-11-yl]piperazin-1-yl}propanoic acid dihydrochloride | 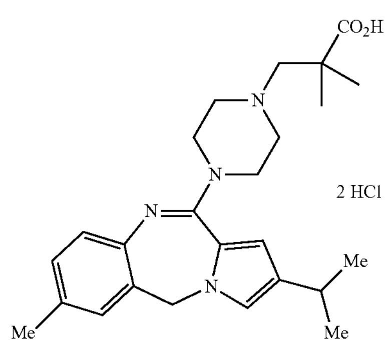 | 423.18 |

-continued

| Example No. | Name | Structure | MS (m/z): (M + 1). |
|---|---|---|---|
| 22 | 3-[4-(2-Ethyl-7-methyl-5H-pyrrolo[2,1-c][1,4]benzodiazepin-11-yl)piperazin-1-yl]-2,2-dimethylpropanoic acid dihydrochloride | 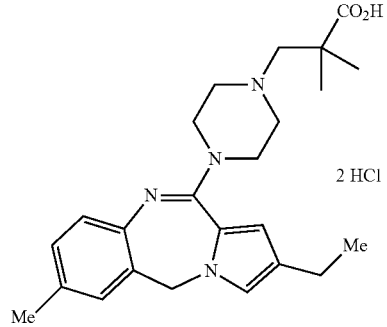 | 409.18 |
| 23 | 3-{4-[7-Chloro-2-(propan-2-yl)-5H-pyrrolo[2,1-c][1,4]benzodiazepin-11-yl]piperazin-1-yl}-2,2-dimethylpropanoic acid dihydrochloride | 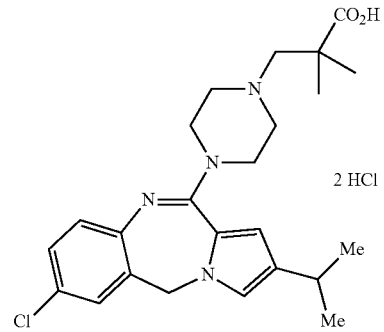 | 443.18 |
| 24 | 2,2-Dimethyl-3-{4-[7-methyl-2-(methylsulfanyl)-5H-pyrrolo[2,1-c][1,4]benzodiazepin-11-yl]piperazin-1-yl}propanoic acid dihydrochloride | 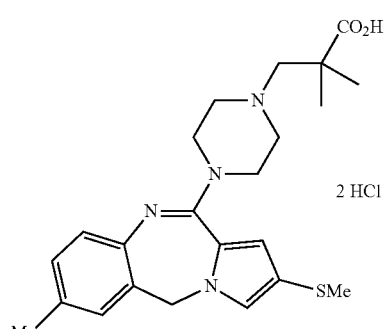 | 427.18 |

EXAMPLE 25

Synthesis of 3-[4-(2-chloro-7-methyl-5H-pyrrolo[2,1-c][1,4]benzodiazepin-11-yl)piperazin-1-yl]-2,2-dimethylpropanoic acid dihydrochloride

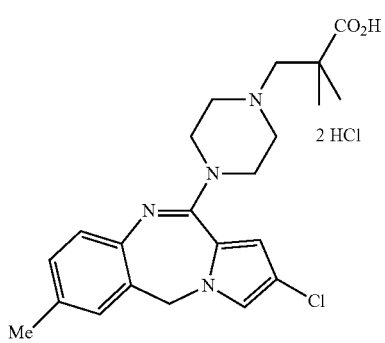

Dissolve methyl 2,2-dimethyl-3-(piperazin-1-yl)-propanoate dihydrochloride (1.49 g, 5.47 mmoles) in water and absorb onto an SCX2 column. Wash the column with methanol and elute methyl 2,2-dimethyl-3-piperazin-1-yl-propanoate with 2M ammonia in methanol. Remove the methanol in vacuo and add the methyl 2,2-dimethyl-3-(piperazin-1-yl)propanoate to acetonitrile (12 mL). Add 2,11-dichloro-7-methyl-5H-pyrrolo[2,1-c][1,4]benzodiazepine (0.85 g, 3.22 mmoles) and sodium bicarbonate (0.405 g, 4.83 mmoles) to the acetonitrile solution. Heat and stir in the microwave for 30 minutes at 140° C. Cool to room temperature, absorb the reaction mixture onto silica and purify by chromatography (gradient elution with EtOAc/isohexane 0:100% to 100:0%). Collect the fractions containing product and evaporate the solvent in vacuo and dissolve the residue in methanol (10 mL) and add lithium hydroxide (0.235 g, 9.65 mmoles). Heat and stir the methanolic solution in the microwave for 12.5 minutes at 140° C. Cool to room temperature and acidify with acetic acid and then evaporate the solvent under reduced pressure. Dissolve the residue in excess 2M HCl (aq) and then evaporated to dryness. Dissolve the residue in water and immobilise onto a macroporous polystyrene hydrogen carbonate (PL-HCO₃) resin. Wash the resin with water and elute from the resin with 2M HCl (aq). Evaporate the solution to dryness to give 3-[4-(2-chloro-7-methyl-5H-pyrrolo[2,1-c][1,4]benzodiazepin-11-yl)piperazin-1-yl]-2, 2-dimethylpropanoic acid dihydrochloride (0.177 g; 11.28% yield). MS (m/z): 415.18 (M+1).

The following compounds are prepared essentially by the method of Example 25.

| Example No. | Name | Structure | MS (m/z): (M + 1). |
|---|---|---|---|
| 26 | 3-[4-(7-Chloro-1-methoxy-2-methyl-5H-pyrrolo[2,1-c][1,4]benzodiazepin-11-yl)piperazin-1-yl]-2,2-dimethylpropanoic acid dihydrochloride | 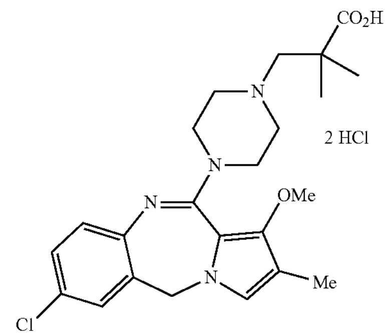 | 445.18 |
| 27 | 3-[4-(1-Methoxy-2,7-dimethyl-5H-pyrrolo[2,1-c][1,4]benzodiazepin-11-yl)piperazin-1-yl]-2,2-dimethylpropanoic acid dihydrochloride | 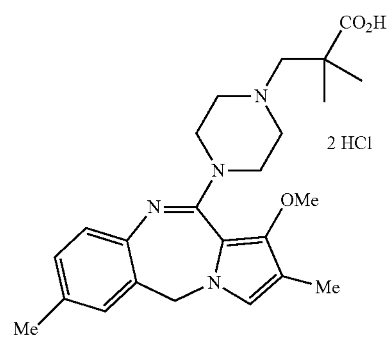 | 425.18 |
| 28 | 3-[4-(2-Bromo-7-methyl-5H-pyrrolo[2,1-c][1,4]benzodiazepin-11-yl)piperazin-1-yl]-2,2-dimethylpropanoic acid dihydrochloride | 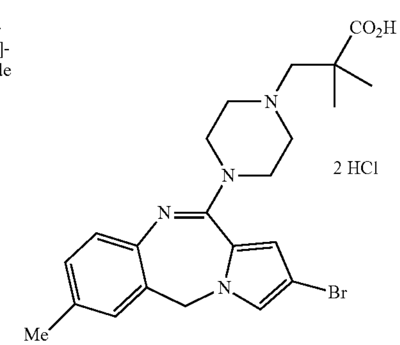 | 459.07, 461.07 |

EXAMPLE 29

Synthesis of Sodium 3-[4-(7-chloro-2-ethyl-5H-pyrrolo[2,1-c][1,4]benzodiazepin-11-yl)piperazin-1-yl]-2,2-dimethylpropanoate

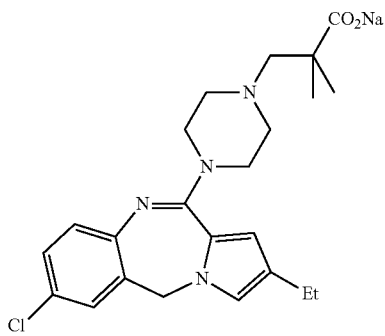

Dissolve 3-[4-(7-chloro-2-ethyl-5H-pyrrolo[2,1-c][1,4]benzodiazepin-11-yl)piperazin-1-yl]-2,2-dimethylpropanoic acid dihydrochloride (201 mg, 400 μmoles in water and methanol (5 mL) then load on to a SCX-2 cartridge (2 g). Wash with methanol and then elute with ammonia in methanol. Concentrate the basic solution to dryness to give 3-[4-(7-chloro-2-ethyl-5H-pyrrolo[2,1-c][1,4]benzodiazepin-11-yl)piperazin-1-yl]-2,2-dimethylpropanoic acid (160 mg, 373 μmoles). Then treat with 2N sodium hydroxide (187 μL, (373 μmoles) and water (3 mL) to cause solution. Then freeze-dry to yield sodium 3-[4-(7-chloro-2-ethyl-5H-pyrrolo[2,1-c][1,4]benzodiazepin-11-yl)piperazin-1-yl]-2,2-dimethylpropanoate (164 mg, 98% yield). MS (m/z): 429.18 (M+1).

EXAMPLE 30

Synthesis of 3-[4-(7-Chloro-2-methyl-5H-pyrrolo[2,1-c][1,4]benzodiazepin-11-yl)piperazin-1-yl]-2,2-dimethylpropanoic acid di-methanesulfonate

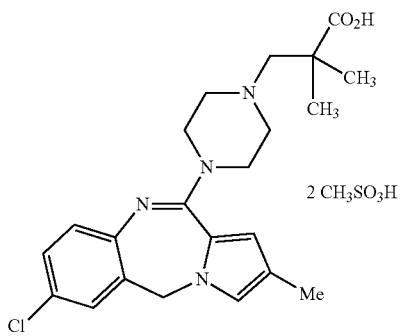

Add acetonitrile (5 mL) to 3-[4-(7-chloro-2-methyl-5H-pyrrolo[2,1-c][1,4]benzodiazepine-11-yl)piperazin-1-yl]-2,2-dimethylpropanoic acid (0.106 g, 0.255 mmol) to create a slurry. Add methanesulfonic acid (0.050 ml, 0.075 g, 0.76 mmol) to the stirring slurry (1000 rpm) and stir the resultant solution at 60° C. until a white solid precipitates. Cool this slurry, and isolate the solid by filtration to obtain 3-[4-(7-chloro-2-methyl-5H-pyrrolo[2,1-c][1,4]benzodiazepin-11-yl)piperazin-1-yl]-2,2-dimethylpropanoic acid di-methanesulfonate (0.15 g).

Literature data (Morairty S R, Hedley L, Flores J, Martin R, Kilduff T S. (2008) Selective 5-$HT_{2A}$ and 5-$HT_6$ receptor antagonists promote sleep in rats. Sleep 31, 34-44; and Barbier, A. J., and Bradbury, M. J., Histaminergic Control of Sleep-Wake Cycles: Recent Therapeutic Advances for Sleep and Wake Disorders, CNS & Neurological Disorders—Drug Targets, vol 6, pg. 31-43 (2007)) and data generated in non-clinical animal studies support a role for dual activity H1 inverse agonists/5-$HT_{2A}$ antagonists in the treatment of insomnia and in the symptomatic treatment of insomnia associated with other disorders such as depressive disorders, anxiety disorders, pain, allergies, lung or airway disorders, psychiatric disorders, dementia, and/or neurodegenerative diseases, and/or circadian rhythm sleep disorders. Specifically it is found that certain dual activity H1 inverse agonists/5-$HT_{2A}$ antagonists are effective in increasing total sleep time using EEG monitored rodents without disproportionate or clinically relevant hypoactivity, decrease in REM sleep, or hypersomnolence.

To further demonstrate the characteristics of the present compounds, compounds may be run in the following in vitro and in vivo assays:

In Vitro Binding and Activity Assays:

H1 Competition Binding Assay

[$^3$H]-Pyrilamine binding experiments are carried out in SPA (scintillation proximity assay) 96-well format. Membranes used in this assay are prepared from HEK-293 cells stably expressing recombinant H1 receptor (human). The incubation is initiated by the addition of a mixture of WGA PVT SPA beads (1 mg/well, Perkin Elmer (MA, USA) RPNQ0001) and 3 μg membranes to assay buffer (67 mM Tris; pH 7.6) containing 3.5 nM [$^3$H]-Pyrilamine and varying concentrations of the test compound (10 point concentration response curves). Non-specific binding is determined in the presence of 10 μM Triprolidine. Samples are incubated for four hours at room temperature (22° C.) and then read in a Microbeta Trilux.

5-$HT_2$ Competition Binding Assay

[$^3$H]-Ketanserin binding experiments are carried out in SPA 96-well format. Membranes used in this assay are prepared from AV-12 cells stably expressing recombinant 5-$HT_{2A}$ receptor (human). The incubation is initiated by the addition of a mixture of WGA YSi SPA beads (1 mg/well, Perkin Elmer (MA, USA), RPNQ0011) and 2 μg membranes to assay buffer (67 mM Tris, 0.5 mM EDTA; pH 7.6) containing 3.1 nM [$^3$H]-Ketanserin and varying concentrations of the test compound (10 point concentration response curves). Non-specific binding is determined in the presence of 20 μM 1-(1-Naphthyl)piperazine. Samples were incubated for four hours at room temperature (22° C.) and then read in a Microbeta Trilux.

5-$HT_{2C}$ Competition Binding Assay

[$^{125}$I]-(±)DOI binding experiments are carried out in SPA 96-well format. Membranes used in this assay are prepared from AV-12 cells stably expressing recombinant 5-$HT_{2c}$ receptor (human). The incubation is initiated by the addition of a mixture of WGA PVT SPA beads (0.5 mg/well, Perkin Elmer (MA, USA), RPNQ0001) and 2.5 μg membranes to assay buffer (50 mM Tris-HCl, 10 mM $MgCl_2$, 0.5 mM EDTA, 10 μM pargyline, 0.1% ascorbic acid, pH7.4) containing 0.2 nM [[$^{125}$I]-(±)DOI and varying concentrations of the test compound (10 point concentration response curves). Non-specific binding is determined in the presence of 20 μM 1-(1-Naphthyl)piperazine. Samples are incubated for four hours at room temperature (22° C.) and then read in a Microbeta Trilux.

Binding Data Analysis

Curves are evaluated using a 4-parameter logistic nonlinear equation to obtain the concentration of competitor causing 50% inhibition of radioligand binding ($IC_{50}$). Equilibrium dissociation constants ($K_i$) are calculated according to the equation $K_i = IC_{50}/(1+L/K_d)$, where L equals the concentration of radioligand used in the experiment and $K_d$ equals the equilibrium dissociation constant of the radioligand for the receptor, determined from standard saturation analysis or homologous competition experiments. Reported values for $K_i$, where n values are indicated, are shown as geometric mean±the standard error of the mean (SEM), with the number of replicate determinations indicated by n. Geometric means are calculated by the equation GeoMean=10^(Average (log $K_i$ 1+log $K_i$ 2+ . . . log $K_i$ n)/sqrt n).

GABA$_A$ Antagonism Using Native Receptors in Primary Neuronal Cultures

Activity of compounds on native GABA$_A$ receptors is evaluated by monitoring calcium fluxes using a 96 well format FLIPR® system (Fluorometric Imaging Plate Reader (FLIPR®, Molecular Devices). Briefly, cortical embryonic neurons are dissociated from E18 rat embryos and plated at optimum density into black-walled, transparent bottom poly-D-lysine coated 96-well FLIPR® plates. After loading the cells with a calcium sensitive dye (Fluo-4-AM, Molecular Devices), the cells are bathed in a solution containing low chloride (chloride replaced by gluconate). Under these conditions activation of GABA$_A$ receptors causes an efflux of chloride ions (in the direction of the chemical gradient), which results in membrane depolarization and consequently activation of voltage gated calcium channels (VGCCs). Calcium influx through VGCCs is recorded and analysed offline using the FLIPR® system. For a pharmacological validation of the assay, concentration response curves (CRC) are recorded for the standard agonist (GABA) and standard antagonist (Gabazine). Any effects are determined in CRC mode against a fixed concentration of agonist GABA at 10 μM (equivalent to an $EC_{90}$ GABA response).

Methods:

The antagonist effects of compounds are quantified using 10-point dose response curves by comparing the peak fluorescent responses to the agonist GABA in the presence and absence of compound. The assay window is defined as the maximal response obtained by GABA at its predetermined $EC_{90}$ concentration minus the response obtained by a fully inhibiting concentration of gabazine (50 μM). Antagonist effects are calculated as a percent of the assay window. All data are calculated as relative $IC_{50}$ values using a four-parameter logistic curve fitting program (Prism Graphpad® 3.01). Antagonist potencies for all compounds are compared to gabazine with three replicates in each assay run.

Exemplified compounds or exemplified salts thereof are tested essentially as described above and are found to have high affinity for the H1 and 5-HT$_{2A}$ receptors and selectivity over the 5-HT$_{2C}$ receptor. $K_i$'s for the H1 and 5-HT$_{2A}$ receptors for the exemplified compounds are found to be less than 100 nM and 200 nM, respectively, while the $K_i$'s for the 5-HT$_{2C}$ receptor are found to be greater then 1000 nM.

Further, the compounds of the invention may be tested in binding assays and functional activity assays by well known methods for other physiologically important receptors such as, but not limited to, the hERG channel, other serotonin receptors (specifically 5-HT$_{1A}$, 5-HT$_{1B}$, 5-HT$_{1D}$, 5-HT$_{1E}$, 5-HT$_{1F}$ receptors, lack of agonist activity at 5-HT$_{2B}$ receptors, 5-HT$_{2C}$, 5-HT$_4$, 5-HT$_5$, 5-HT$_6$, and 5-HT$_7$ receptors), muscarinic receptors, dopaminergic receptors (specifically D1, D2, and D3), GABA$_A$ receptors, adrenergic receptors and monoamine transporters. Certain exemplified compounds are tested at these receptors and are shown to lack significant activity.

The compounds of examples 1 and 13 are tested essentially as described above and are found to have activity profiles as shown in Table 1.

TABLE 1

| Selectivity data | | |
|---|---|---|
| | Example 1 | Example 13 |
| H1 $K_i$ (nM) | 27.3 | 16.8 |
| 5-HT$_{2A}$ $K_i$ (nM) | 57.5 | 63.2 |
| 5-HT$_{2B}$ Agonist $EC_{50}$ (nM) | >10000 | >10000 |
| 5-HT$_{2C}$ $K_i$ (nM) | 3810 | 2370 |
| GABA$_A$ $IC_{50}$ (μM) | — | >50 |
| hERG Channel (μM) | >100 | >100 |
| Dopamine D$_1$ $K_i$ (nM) | 3790 | 1860 |
| Dopamine D$_2$ $K_i$ (nM) | >4500 | 3420 |
| Dopamine D$_3$ $K_i$ (nM) | >5680 | >4110 |
| 5-HT$_{1A}$ $K_i$ (nM) | >6940 | — |
| 5-HT$_{1B}$ $K_i$ (nM) | >5580 | >5580 |
| 5-HT$_{1D}$ $K_i$ (nM) | >3980 | >8550 |
| 5-HT$_{1E}$ $K_i$ (nM) | — | >5370 |
| 5-HT$_{1F}$ $K_i$ (nM) | — | >8250 |
| 5-HT$_5$ $K_i$ (nM) | >8830 | >9090 |
| 5-HT$_6$ $K_i$ (nM) | 2690 | >5830 |
| 5-HT$_7$ $K_i$ (nM) | >2060 | >3970 |
| Adrenergic alpha$_{1A}$ $K_i$ (nM) | >8910 | >8910 |
| Adrenergic alpha$_{1B}$ $K_i$ (nM) | >10900 | >10900 |
| Adrenergic alpha$_{2A}$ $K_i$ (nM) | >9030 | >8470 |
| Adrenergic alpha$_{2B}$ $K_i$ (nM) | >4980 | >4800 |
| Adrenergic alpha$_{2C}$ $K_i$ (nM) | >4020 | >5330 |
| Serotonin Transporter | >641 | >515 |
| Norepinephrine Transport | >682 | >526 |
| Dopamine Transporter | >879 | >880 |

Therefore, physiologically relevant doses of the compounds of the invention are expected to provide substantial inhibition of H1 and 5-HT$_{2A}$ receptors in vivo, while not substantially interacting with other physiologically relevant receptors, and thus are expected to provide the desired pharmacology while avoiding undesired effects associated with off-target activity. Such undesired effects include, but are not limited to the following: 5-HT$_{2C}$ antagonist activity associated with treatment emergent weight gain, 5-HT$_{2B}$ agonist activity associated with valvulopathy, hERG channel modulation associated with QT prolongation, and GABA$_A$ activity associated with seizure activity. Furthermore, interference with sleep/wake physiology is avoided by the selectivity over dopamine receptors, other serotonin receptors, adrenergic receptors, and monoamine transporters.

5-HT$_{2A}$ Receptor Occupancy Receptor occupancy is assayed to demonstrate the extent of interaction with the 5-HT$_{2A}$ Receptor in vivo. Briefly, male Sprague-Dawley rats (Harlan Sprague-Dawley, Indianapolis, Ind.) weighing approximately 230-280 grams are given ad lib access to food and water until the beginning of the 3-hour experimental protocol. 1 mg/kg ketanserin (non-selective 5-HT$_{2A}$ antagonist) is used as a positive control to establish assay validity. Test compounds or control are administered by oral gavage in a vehicle comprised of 20% hydroxypropyl beta-cyclodextrin. MDL 100907 ((R) -(+)-α-(2,3-Dimethoxyphenyl)-1-[2-(4-fluorophenyl)ethyl]-4-piperidinemethanol), a selective 5-HT$_{2A}$ antagonist, is used as a tracer. MDL 100907 is suspended in water with 5 μl dilute lactic acid (1 mg/ml), diluted to 6 μg/ml with saline, and administered in a volume of 1 mL/kg intravenously via the lateral tail vein to yield a tracer dose of 3 μg/kg. Rats are administered test compound, ketanserin, or vehicle (N=4), followed one hour later with an intravenous, 3

µg/kg tracer dose of MDL 100907. It is at the time of tracer administration that receptor occupancy (RO) is considered to be measured. Fifteen minutes after tracer administration, rats are sacrificed by cervical dislocation. Plasma samples are collected and samples of the frontal cortex and cerebellum are removed. The level of MDL 100907 tracer is measured in each cortical and cerebellar sample. RO is calculated using the well-established ratio method which employs a region of high receptor density representative of total binding (frontal cortex) normalized by an area without or with very low levels of receptor (cerebellum). This region, referred to as the null region, represents nonspecific binding of the ligand probe. Vehicle ratio of the tracer levels in cortex relative to cerebellum represents 0% occupancy. A ratio of 1 represents 100% occupancy and is achieved when all specific binding to the 5-$HT_{2A}$ receptor of the MDL 100907 tracer is blocked. The intermediate ratios of cortical to cerebellar tracer from the test compound pretreated group are interpolated linearly between the ratio of tracer levels in the vehicle-treated animals (0% occupancy) and a ratio of 1 (100% occupancy) in order to determine the percent 5-$HT_{2A}$ RO.

MDL 100907 Analysis: Cortex and cerebellar samples are weighed and placed in conical centrifuge tubes on ice. Four volumes (w/v) of acetonitrile containing 0.1% formic acid is added to each tube. The samples are then homogenized and centrifuged at 14,000 RPM (21,920×g) for 16 minutes. Supernatant is diluted by adding 100-900 µL, sterile water in HPLC injection vials for LC/MS/MS analysis. Analysis of MDL 100907 is carried out using an Agilent model 1200 HPLC (Agilent Technologies, Palo Alto, Calif.) and an API 4000 mass spectrometer. The chromatographic separation is on a 2.1×50 mm C18 column (Agilent part number 971700-907) with a mobile phase consisting of 60% acetonitrile in water with an overall 0.1% formic acid content. Detection of MDL 100907 is accomplished by monitoring the precursor to product ion transition with a mass to charge ratio (m/z) of 374.2 to 123.0. Standards are prepared by adding known quantities of analyte to brain tissue samples from non-treated rats and processing as described above.

Statistical Methods: Curves for each study are fitted to a 4 parameter logistic function with the bottom fixed at 0% using JMP® version 8.0 (SAS Institute Inc, Cary N.C.) and the absolute $ED_{50}$ is calculated by the software. Values are given as means, standard errors and 95% confidence intervals. The compound of Example 13 is tested essentially as described and is found to achieve high 5-$HT_{2A}$ receptor occupancy with an $EC_{50}$ of 0.27 mg/kg (SE=0.069, 95% CI=0.16-0.48 mg/kg).

Histamine H1 Receptor Occupancy: H1 RO is assayed to demonstrate the extent of interaction with the H1 receptor in vivo. Briefly, male Sprague-Dawley rats (Harlan Sprague-Dawley, Indianapolis, Ind.) weighing approximately 230-280 grams are given ad lib access to food and water until the beginning of the 3-hour experimental protocol. 3-[4-(8-Fluorodibenzo[b,f][1,4]oxazepin-1'-yl)piperazin-1-yl]-2,2-dimethylpropanoic acid dihydrochloride is used as a positive control and doxepin is used as a tracer. Test compounds and control are administered by oral gavage in a vehicle comprised of 20% hydroxypropyl beta-cyclodextrin. Doxepin is dissolved in sterile water (100 µg/ml), diluted to 2 µg/ml with saline, and administered in a volume of 0.5 mL/kg intravenously via the lateral tail vein to yield a tracer dose of 1 µg/kg. Rats are administered test compound, 15 mg/kg positive control, or vehicle, followed 1 hour later by an intravenous "tracer" dose of doxepin (N=4). It is at the time of tracer administration that RO is considered to be measured. 40 mins after tracer administration, rats are sacrificed by cervical dislocation. Plasma samples are collected and the frontal cortex is removed. The level of doxepin tracer is measured in each cortical sample. RO is calculated using a within tissue comparison of tracer levels under vehicle conditions (0% occupancy) and positive control conditions (100% occupancy). 15 mg/kg of positive control administered intravenously with a 30 minute pretreatment is predetermined to represent full blockade of specific binding of the tracer to H1 receptors. Additional treatment groups with doses of test compound are linearly interpolated between the vehicle and positive control groups to calculate percent H1 RO.

Doxepin Analysis: Cortical samples are weighed and placed in conical centrifuge tubes on ice. Four volumes (w/v) of acetonitrile containing 0.1% formic acid is added to each tube. The samples are homogenized and centrifuged using a at 14,000 RPM (21,920×g) for 16 minutes. Supernatant is diluted with 100-900 µL sterile water in HPLC injection vials for LC/MS/MS analysis. LC/MS/MS analysis of doxepin was carried out using an Agilent model 1200 HPLC (Agilent Technologies, Palo Alto, Calif.) and an API 4000 mass spectrometer. The chromatographic separation employed a 2.1× 50 mm C18 column (Agilent part number 971700-907) and a mobile phase using a gradient method consisting of initial conditions of 10% acetonitrile (ACN) in water with an overall 0.1% formic acid content, after 1 min.-10% ACN, 2 min.-90% ACN, 2.9 min.-90% ACN, 3.1 min.-10% ACN, 5.5 min.-Stop. Detection of doxepin was accomplished by monitoring the precursor to product ion transition with a mass to charge ratio (m/z) of 280 to 107.1. Standards are prepared by adding known quantities of analyte to brain tissue samples from non-treated rats and processing as described above.

Statistical Methods: Curves are fitted to a 4 parameter logistic (none held constant) using Prism® version 3.02 (GraphPad Software, San Diego, Calif.) and the relative $ED_{50}$ is calculated by the software. Values are given as means±the standard error of the mean. The compound of Example 13 is tested essentially as described and is found to achieve high H1 RO with an $EC_{50}$ of 0.3 mg/kg.

H1 Inverse Agonism: To determine the inverse agonist nature of compounds of the present invention, their effects on the levels of Myo-Inositol 1 phosphate (IP1) in HEK293 cells transfected with the human recombinant H1 receptor (HEK293/hm H1 clone R-40) are measured. Briefly, HEK293/hm H1 cells (clone R-40) are grown to ~90% confluency (3:1 DMEM/F12, 5% FBS, 20 mM HEPES, G418 500 pg/ml, 1% Pen/Strep/Glutamine) and harvested on the day of the assay using 1× Trypsin/EDTA (PAA Pasching, Austria L11-003). 35 µl cells (300K) are seeded into 96 W half area white solid bottom plates (Corning, UK 3688) in stimulation buffer (NaCl 146 mM, $CaCl_2$ 1 mM, KCl 4.2 mM, $MgCl_2$ 0.5 mM, Glucose 5.5 mM, HEPES 10 mM and LiCl 50 mM). Test compounds are initially dissolved in 100% DMSO at 1 mM, and serially diluted (half log) in 100% DMSO to give 10 point dose response curves (Biomek 2000, Beckman Coulter UK). These are further diluted to ×2 final assay concentration in stimulation buffer using the Cybiwell (CiBio Jena, Germany) and 35 µl added to the cells in the assay plate (10 µM maximum final concentration). Cells plus compound are incubated for 1 hour 30 mins at 37'C/5% $CO_2$ before addition of 15 µl of each of the HTRF IP1 detection kit reagents (CisBio 62P1APEC). The cell plate is incubated for a further hour at room temperature before measuring IP 1 accumulation (Envision plate reader, Perkin Elmer). IP 1 accumulation (nM) is calculated by extrapolation from the standard IP1 curve run on the day of the assay. $EC_{50}$ values are calculated using a 4-parameter curve fit (Graph Pad Prism v3.02). Negative efficacy values are expressed relative to the positive control Tripelennamine (10 μM, Sigma, UK P5514). Representative compounds of the present invention are assayed essentially as described and are found to be inverse agonists at the H1 receptor. Compound 13 is tested essentially as described and is found to fully suppress constitutive activity (126±6%) with an $IC_{50}$ of 53.9±37 nM.

Inhibition of DOI Induced Headshake Activity: The in vivo $5-HT_{2A}$ receptor antagonist activity of the compounds of the present invention is demonstrated by their ability to block head shaking activity induced by the $5-HT_{2A}$ receptor agonist 2,5-dimethoxy-4-iodoamphetamine (DOI). (see for example Bartoszyk G D, van Amsterdam C, Böttcher H, Seyfried C A. EMD 281014, a new selective serotonin $5-HT_{2A}$ receptor antagonist. *Eur J Pharmacol.* 2003 473: 229-230.) Briefly, male C57BL/6J mice (20-25 g, Charles River) are housed in standard housing conditions (32 mice in a large IVC cage, 07.00 to 19.00 light phase, constant temperature (19-23° C.) and humidity (50%+/−10), ad lib food and water). Mice received either vehicle (0.25% Methyl cellulose), DOI (3 mg/kg in saline) or test compound at 10 mg/kg PO plus DOI (3 mg/kg in saline). Test compounds are individually evaluated in groups of four per experiment with n=4 for each compound, together with vehicle and DOI+vehicle (n=8). After a test compound pre-treatment time of 60 minutes the mice receive either vehicle (saline) or 3 mg/kg DOI dosed subcutaneously, and are then placed into clear perspex observation chambers. Five minutes after DOI or vehicle administration the number of visually scored head shakes exhibited by each individual mouse is counted for 15 minutes. The data is analyzed using an ANOVA and post-hoc Dunnet's Test. Exemplified compounds are tested essentially as described and are found to inhibit the DOI induced headshake response at greater than 90% at 10 mg/kg. The compound of example 13 is tested essentially as described and is found to inhibit the DOI induced headshake response at 100% at 10 mg/kg.

Sleep and behavioral monitoring in rats: Representative compounds of the present invention are tested in rats for their ability to increase the amount of sleep or decrease sleep interruption or both without undesired effects such as inhibition of REM sleep, waking motor impairment, and/or rebound insomnia. Test animals are continuously monitored by electro-encephalograms (EEG), electromyograms (EMG), and motion to measure cumulative nonREM sleep, cumulative total sleep, average sleep bout duration, longest sleep bout duration, rebound insomnia, REM sleep inhibition and locomotor activity intensity during wakefulness. Methods for such studies are known in the art (see for example methods described in Edgar D M, Seidel W F. Modafinil induces wakefulness without intensifying motor activity or subsequent rebound hypersomnolence in the rat. *J Pharmacology & Experimental Therapeutics* 1997; 283: 757-769; van Gelder R N, Edgar D M, Dement W C. Real-time automated sleep scoring: validation of a microcomputer-based system for mice. Sleep 1991, 14: 48-55; and Gross B A, Walsh C M, Turakhia A A, Booth V, Mashour G A, Poe G R. Open-source logic-based automated sleep scoring software using electrophysiological recordings in rats. *J Neurosci Methods.* 2009; 184(1):10-8.) Studies are conducted as follows:

Animal preparation. Adult, male Wistar rats (approximately 270-300 g at time of surgery) are surgically fitted for chronic recording of EEG, EMG, and motion as follows: Rats are surgically prepared with a cranial implant consisting of four stainless steel screws for EEG recording (two frontal [3.9 mm anterior from bregma, and ±2.0 mm mediolaterally] and two occipital [6.4 mm posterior from bregma, ±5.5 mm mediolaterally]), and with two Teflon-coated stainless steel wires for EMG recording (positioned under the nuchal trapezoid muscles). All leads are soldered to a miniature connector (Microtech, Boothwyn, Pa.) prior to surgery. The implant assembly is affixed to the skull by the combination of the stainless steel EEG recording screws, cyanoacrylate applied between the implant connector and skull, and dental acrylic. Locomotor activity is monitored via a miniature transmitter (Minimitter PDT4000G, Philips Respironics, Bend, Oreg.) surgically placed into the abdomen. At least 3 weeks are allowed for recovery.

Recording environment. Each rat is housed individually within a microisolator cage modified with an inserted polycarbonate filter-top riser to allow more vertical headroom. A flexible cable that minimally restricts movement is connected at one end to a commutator affixed to the cage top and at the other end to the animal's cranial implant. Each cage is located within separate, ventilated compartments of a stainless steel sleep-wake recording chamber. Food and water are available ad libitum and the ambient temperature is maintained at about 23±1° C. A 24-hr. light-dark cycle (LD 12:12) using fluorescent light is maintained throughout the study. Relative humidity averages approximately 50%. Animals are undisturbed for at least 30 hrs before and after each treatment.

Study design and dosing. The vehicle (placebo, methylcellulose 15 centipoise 0.25% in water) or one of the test compound dose levels is administered orally at 1 mL/kg pseudo-randomly such that no rat receives the same treatment twice, and no rat receives more than two of the 8 treatments in any one study. Each rat is removed from its cage for about a minute to be weighed and treated. At least 6 days "washout" period precede and follow each treatment.

Data collection. Sleep and wakefulness discrimination may be automated (e.g., Van Gelder et al. 1991 (above); Edgar et al. 1997 (above); Winrow C J, et al., *Neuropharmacology* 2010; 58(1):185-94.; and Gross et al., 2009 (above). EEG is amplified and filtered (X10,000, bandpass 1-30 Hz), EMG is amplified and integrated (bandpass 10-100 Hz, RMS integration), and non-specific locomotor activity (LMA) is monitored simultaneously. Arousal states are classified in 10 second epochs as non-REM sleep, REM sleep, wakefulness, or theta-dominated wakefulness. Locomotor activity (LMA) is recorded as counts per minute and is detected by commerically available telemetry receivers (ER4000, Minimitter, Bend, Oreg.).

Statistical Analysis. All animals having at least one outcome are included in the summary results (for example, we include appropriate data from an animal treatment for which telemetry data is usable but EEG data is not). The post-treatment observation period is divided into post-dosing intervals appropriate to each Outcome, where the time of dosing is defined as the start of Hour=0, and outcomes are summarized in the observation period by computing either the mean hourly or the cumulative value across each period (see legend of Table 1 for precise definition of each Outcome). Sleep bouts are analyzed on the log scale to stabilize the variation, all other variates are analyzed on the linear scale. Each outcome in each period is analyzed by analysis of covariance using treatment group and treatment date as factors and the corresponding pre-treatment interval, 24 hrs earlier, as the covariate. Adjusted means and the change from vehicle means and their corresponding standard errors are summarized for each treatment group. Outcomes analyzed on the log scale are back-transformed to report geometric means and mean ratio-to-vehicle results.

The compounds of Examples 13-28 are tested essentially as described. The compounds of Examples 13, 15, 16, 18 and 19 are found to significantly increase cumulative NREM sleep time and cumulative total sleep time without significant rebound insomnia, REM sleep inhibition or inhibition of locomotor intensity (LMI) at 3 mg/kg. The compound of Example 13 is tested essentially as described and is found to have the sleep profile and locomotor activity intensity as shown in Table 2.

TABLE 2

Compound of Example 13.

| | Efficacy variables Cumulative NREM sleep | | | Undesired effect variables Rebound Insomnia | | |
|---|---|---|---|---|---|---|
| Dose (mg/kg PO) | N | Adj. Mean | SE | N | Adj. Mean | LCL |
| 10 | 10 | 51.8 | 6.5 | 10 | 3.1 | −6.1 |
| 3 | 14 | 39.5 | 5.5 | 14 | −7.8 | −15.8 |
| 1 | 14 | 28.0 | 5.5 | 14 | −9.7 | −17.7 |
| 0.50 | 15 | 22.2 | 5.3 | 15 | −7.2 | −15.1 |
| 0.25 | 15 | 15.2 | 5.4 | 15 | −1.9 | −9.7 |
| 0.10 | 5 | 5.9 | 8.1 | 5 | −5.4 | −17.2 |
| 0.03 | 9 | 5.1 | 6.4 | 9 | −0.7 | −10.1 |

| | Cumulative Total sleep | | | REM inhibition | | |
|---|---|---|---|---|---|---|
| Dose (mg/kg PO) | N | Adj. Mean | SE | N | Adj. Mean | LCL |
| 10 | 10 | 52.8 | 7.3 | 10 | 2.9 | −4.6 |
| 3 | 14 | 42.3 | 6.2 | 14 | 7.0 | 0.7 |
| 1 | 14 | 30.6 | 6.1 | 14 | 2.6 | −3.7 |
| 0.50 | 15 | 25.1 | 6.0 | 15 | 5.8 | −0.5 |
| 0.25 | 15 | 17.7 | 6.1 | 15 | 4.7 | −1.7 |
| 0.10 | 5 | 5.9 | 9.0 | 5 | 1.0 | −8.0 |
| 0.03 | 9 | 7.3 | 7.2 | 9 | 1.8 | −5.8 |

| | Average Sleep Bout | | | Locomotor Activity Intensity | | |
|---|---|---|---|---|---|---|
| Dose (mg/kg PO) | N | Adj. Mean | SE | N | Adj. Mean | LCL |
| 10 | 10 | 2.3 | 0.3 | 10 | −0.11 | −3.09 |
| 3 | 14 | 1.8 | 0.2 | 13 | −1.49 | −4.19 |
| 1 | 14 | 1.6 | 0.2 | 10 | −2.94 | −5.87 |
| 0.50 | 15 | 1.4 | 0.1 | 14 | −0.14 | −2.75 |
| 0.25 | 15 | 1.2 | 0.1 | 12 | −0.58 | −3.30 |
| 0.10 | 5 | 1.1 | 0.2 | 5 | −0.35 | −4.29 |
| 0.03 | 9 | 1.1 | 0.1 | 9 | −0.97 | −4.07 |

| | Longest Sleep Bout | | |
|---|---|---|---|
| Dose (mg/kg PO) | N | Adj. Mean | SE |
| 10 | 10 | 3.1 | 0.4 |
| 3 | 14 | 2.7 | 0.3 |
| 1 | 14 | 2.5 | 0.3 |
| 0.50 | 15 | 1.8 | 0.2 |
| 0.25 | 15 | 1.7 | 0.2 |
| 0.10 | 5 | 1.7 | 0.3 |
| 0.03 | 9 | 1.3 | 0.2 |

Table 2. Outcome statistics:
Abbreviations:
N = sample size;
Adj. Mean = adjusted group mean value relative to vehicle controls;
SE = standard error of the mean; LCL = lower 95% confidence limit,
NREM = non-REM, i.e., all sleep other than REM sleep.
Definitions and units - means are adjusted differences from vehicle controls:
Cumulative sleep: across the first 6 hours post-treatment, in minutes ('Total sleep' denotes NREM sleep + REM sleep).
Average sleep bout: average of hourly-averaged sleep bouts, across the first 6 hours post-treatment, expressed as n-fold increase over vehicle controls.
Longest sleep bout: the longest sleep bout in the first 6 hours post-treatment, expressed as n-fold increase over vehicle controls.
Rebound insomnia: cumulative minutes of NREM + REM sleep during the first 3 hours of the lights on period, i.e., $7^{th}$, $8^{th}$ and $9^{th}$ hours post-treatment.
REM inhibition: cumulative minutes of REM sleep during the first 12 hours post-treatment.
Locomotor Activity (LMA) Intensity: expressed as LMA counts per minute of EEG-defined wakefulness, averaged across the first 6 hours post-treatment.

Determining efficacy. The threshold efficacy for each of the four efficacy variables is calculated by plotting the increase in each variable relative to vehicle controls during the 6 hour period after treatment against log(dose). The threshold efficacy for each variable is that dose which gives the defined efficacy threshold value; +30 min. of additional accumulated non-REM sleep, +25 min. of additional accumulated total sleep, 1.75× increase in average sleep bout duration, and 1.5× increase in longest sleep bout duration. The compound of example 13 is found to have threshold efficacious doses as shown in Table 3.

TABLE 3

| | Estimated efficacy dose (mg/kg) | 95% confidence interval (mg/kg) |
|---|---|---|
| NREM accumulation = 30 min | 1.2 | 0.89-1.6 |
| total sleep accumulation = 25 min | 0.58 | 0.40-0.86 |
| longest sleep bout (1.75-fold increase) | 0.21 | 0.098-0.44 |
| average sleep bout (1.5-fold increase) | 0.77 | 0.44-1.4 |

Determining undesired effects. Each 'undesired effect' outcome variable (see Table 4 legend for definitions), is plotted against log(dose).

The threshhold value for REM inhibition is defined as a cumulative reduction of REM sleep of −10 min. The threshold value for rebound insomnia is defined as −20 min. The threshold value for reduced LMI is defined as −5 locomotor activity counts per minute of EEG-defined wakefulness. A significant undesired effect is defined to occur when the lower confidence limit goes below the threshold value; for all doses at or above the average efficacious dose. For Exemplified compounds, no undesired occurances of REM inhibition, rebound insomnia, or reduction in LMI are observed at doses up to at least 10 mg/Kg. (Negative value indicate REM inhibition, rebound insomnia and reduced LMI, respectively).

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., $21^{st}$ ed., Lippincott Williams & Wilkins Co., 2005).

The compositions are preferably formulated in a unit dosage form, each dosage containing from about 0.1 to about 60 mg, more usually about 1 to about 30 mg, as for example between about 2 and about 10 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.002 to about 1.0 mg/kg, more usually from about 0.015 to 0.5 mg/kg, and as for example between 0.03 and 0.15 mg/kg of body weight. In some instances dosage levels below the lower limit of the aforesaid range may be more than adequate, while in other cases still larger doses may be employed without causing any harmful side effect, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula

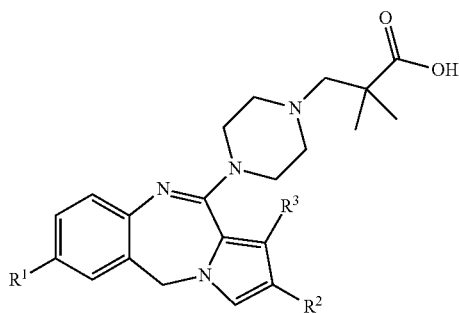

where $R^1$ is chloro or methyl;
$R^2$ is methyl, ethyl, isopropyl, chloro, bromo, trifluoromethyl, or methylthio; and
$R^3$ is hydrogen or methoxy;
or a pharmaceutically acceptable salt thereof.

2. The compound according to claim 1 where $R^3$ is hydrogen, or a pharmaceutically acceptable salt thereof.

3. The compound according to claim 1 where $R^1$ is chloro, or a pharmaceutically acceptable salt thereof.

4. The compound according to claim 1 which is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

5. The compound according to claim 1 which is 3-[4-(7-Chloro-2-methyl-5H-pyrrolo[2,1-c][1,4]benzodiazepin-11-yl)piperazin-1-yl]-2,2-dimethyl-propanoic acid dihydrochloride.

6. A pharmaceutical composition comprising a compound of formula

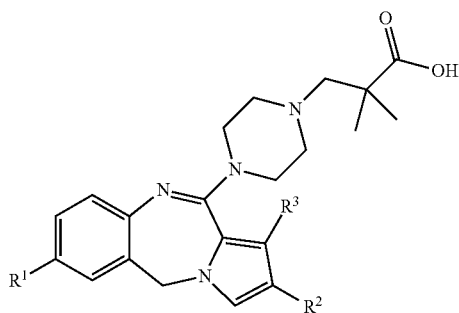

where $R^1$ is chloro or methyl;
$R^2$ is methyl, ethyl, isopropyl, chloro, bromo, trifluoromethyl, or methylthio; and
$R^3$ is hydrogen or methoxy;
or a pharmaceutically acceptable salt thereof, and at least one pharmaceutically acceptable carrier, diluent, or excipient.

7. The pharmaceutical composition of claim 6, wherein the compound is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

8. A method of treating insomnia in a mammal comprising administering to the mammal in need of such treatment an effective amount of a compound of the formula

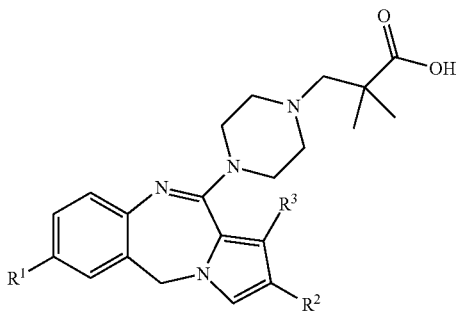

where $R^1$ is chloro or methyl;
$R^2$ is methyl, ethyl, isopropyl, chloro, bromo, trifluoromethyl, or methylthio; and
$R^3$ is hydrogen or methoxy;
or a pharmaceutically acceptable salt thereof.

9. The method of claim 8 where the mammal is a human.

10. The method of claim 8 where the insomnia is characterized by difficulties in sleep onset or sleep maintenance or both.

11. The method of claim 10 where the mammal is a human.

12. The method of claim 8 where the compound is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

13. The method of claim 9 where the compound is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

14. The method of claim 10 where the compound is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

15. The method of claim 11 where the compound is 3-[4-(7-Chloro-2-methyl-5H-pyrrolo[2,1-c][1,4]benzodiazepin-11-yl)piperazin-1-yl]-2,2-dimethylpropanoic acid, or a pharmaceutically acceptable salt thereof.

* * * * *

UNITED STATES PATENT AND TRADEMARK OFFICE
CERTIFICATE OF CORRECTION

PATENT NO. : 8,314,092 B2
APPLICATION NO. : 13/357627
DATED : November 20, 2012
INVENTOR(S) : Anne Marie Camp et al.

It is certified that error appears in the above-identified patent and that said Letters Patent is hereby corrected as shown below:

Cover Page, item (75), Column 1, Line 4, Delete "Berkshire (DE);" and insert -- Berkshire (GB); --, therefor.

Cover Page, Column 2, Line 7, under Other Publications, Delete "Inramolecular" and insert -- Intramolecular --, therefor.

Column 65, Line 40, In Claim 5, delete "dimethyl-propanoic" and insert -- dimethylpropanoic --, therefor.

Signed and Sealed this
Twelfth Day of February, 2013

Teresa Stanek Rea
*Acting Director of the United States Patent and Trademark Office*